(12) United States Patent
McGovern et al.

(10) Patent No.: US 6,517,534 B1
(45) Date of Patent: *Feb. 11, 2003

(54) PERI-URETHRAL ABLATION

(75) Inventors: Francis J. McGovern, Lexington, MA (US); S. Nahum Goldberg, Brookline, MA (US); Eric R. Cosman, Belmont, MA (US); William J. Rittman, III, Lynnfield, MA (US)

(73) Assignees: Cosman Company, Inc., Belmont, MA (US); The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/375,469

(22) Filed: Aug. 15, 1999

Related U.S. Application Data

(63) Continuation-in-part of application No. 09/021,802, filed on Feb. 11, 1998, now Pat. No. 6,440,127, which is a continuation-in-part of application No. 09/113,683, filed on Jul. 10, 1998, now Pat. No. 6,447,505, which is a continuation-in-part of application No. 09/287,589, filed on Apr. 6, 1999, now abandoned.

(51) Int. Cl.[7] .............................................. A61B 18/14

(52) U.S. Cl. ........................ 606/41; 607/99; 607/113; 606/28

(58) Field of Search .............................. 606/41, 49, 50, 606/28, 29; 607/98, 99, 105, 113

(56) References Cited

U.S. PATENT DOCUMENTS

| | | | |
|---|---|---|---|
| 2,407,690 A | 9/1946 | Southworth | 128/422 |
| 4,116,198 A | 9/1978 | Roos | 128/303.15 |
| 4,184,492 A | 1/1980 | Meinke et al. | 128/303.14 |
| 4,411,266 A | 10/1983 | Cosman | 128/303.18 |
| 4,682,596 A | 7/1987 | Bales et al. | 128/303.14 |
| 4,785,823 A | 11/1988 | Eggers et al. | |
| 4,967,765 A | 11/1990 | Turner et al. | 128/785 |

(List continued on next page.)

FOREIGN PATENT DOCUMENTS

| | | | |
|---|---|---|---|
| EP | 0 754 437 A2 | 1/1997 | A61B/17/39 |
| WO | WO 91/13650 | 9/1991 | A61N/5/04 |
| WO | WO 96-00036 | 1/1996 | |
| WO | WO 96-00039 | 1/1996 | |
| WO | WO 96/34571 | 11/1996 | |
| WO | WO 96/37158 | 11/1996 | A61B/17/36 |
| WO | WO 97/00646 | 1/1997 | A61B/17/39 |
| WO | WO 97/00647 | 1/1997 | A61B/17/39 |
| WO | WO 97/28840 | 8/1997 | A61M/25/10 |
| WO | WO 98/27881 | 7/1998 | A61B/17/39 |

OTHER PUBLICATIONS

US 5,326,343, 7/1994, Rudie et al. (withdrawn)
Bhanot, et al. "A Radiofrequency Method of Thermal Tissue Ablation for Benign Prostatic Hyperplasia," *Urology*, Mar. 1995, 45:427–433.
Cosman, et al. "Theoretical Aspects of Radiofrequency Lesions in the Dorsal Root Entry Zone," *Neurosurgery*, 15:945–950 (1984).

(List continued on next page.)

*Primary Examiner*—Lee Cohen
(74) *Attorney, Agent, or Firm*—Fish & Richardson P.C.

(57) ABSTRACT

Relief of urethral obstruction is achieved by heat ablation of prostatic tissue by an ablation probe passed within the urethra to a position in the prostate near the point of urethral obstruction. The probe is coupled to a power supply to deliver power to tissue near the probe and thus to ablatively heat the urethra and the prostatic tissue near the urethra. The temperature of the tissue is sensed at the probe to control the heating and ablation process. In one embodiment, the probe has a blunt tip to help prevent piercing of the wall of the urethra during insertion of the probe into the urethra through the penis and the positioning of the probe tip near to the point of urethral obstruction. Several forms of probes, apparatus, and methods accommodate the specific objectives.

25 Claims, 11 Drawing Sheets

U.S. PATENT DOCUMENTS

| | | | |
|---|---|---|---|
| 4,979,948 A | 12/1990 | Geddes et al. | 606/33 |
| 5,007,437 A | 4/1991 | Sterzer | 428/786 |
| 5,061,266 A | 10/1991 | Hakky | 606/15 |
| 5,112,330 A | 5/1992 | Nishigaki et al. | 606/46 |
| 5,178,620 A | 1/1993 | Eggers et al. | 606/41 |
| 5,220,927 A | 6/1993 | Astrahan et al. | 128/785 |
| 5,249,585 A | 10/1993 | Turner et al. | 607/99 |
| 5,257,977 A | 11/1993 | Eshel | |
| 5,263,931 A | 11/1993 | Miller | 604/96 |
| 5,277,201 A | 1/1994 | Stern | 607/98 |
| 5,300,099 A | 4/1994 | Rudie | 607/101 |
| 5,301,687 A | 4/1994 | Wong et al. | 606/41 |
| 5,304,214 A | 4/1994 | DeFord et al. | 607/105 |
| 5,322,507 A | 6/1994 | Costello et al. | 128/4 |
| 5,330,518 A | 7/1994 | Neilson et al. | 607/101 |
| 5,348,554 A | 9/1994 | Imran et al. | 606/41 |
| 5,370,675 A | 12/1994 | Edwards et al. | 607/101 |
| 5,370,677 A | 12/1994 | Rudie et al. | 607/101 |
| 5,403,311 A | 4/1995 | Abele et al. | 606/49 |
| 5,454,809 A | 10/1995 | Janssen | 606/41 |
| 5,464,437 A | 11/1995 | Reid et al. | 607/101 |
| 5,472,441 A | 12/1995 | Edwards et al. | |
| 5,480,417 A * | 1/1996 | Hascoet et al. | 607/101 |
| 5,486,161 A | 1/1996 | Lax et al. | 604/22 |
| 5,492,529 A | 2/1996 | Neuwirth et al. | |
| 5,509,929 A | 4/1996 | Hascoet et al. | 607/101 |
| 5,520,684 A | 5/1996 | Imran | 606/41 |
| 5,542,915 A | 8/1996 | Edwards et al. | 604/22 |
| 5,545,137 A | 8/1996 | Rudie et al. | 604/96 |
| 5,545,161 A * | 8/1996 | Imran | 606/41 |
| 5,599,294 A | 2/1997 | Edwards et al. | 604/22 |
| 5,599,346 A | 2/1997 | Edwards et al. | 606/41 |
| 5,620,480 A | 4/1997 | Rudie | 607/101 |
| 5,628,770 A | 5/1997 | Thome et al. | 607/101 |
| 5,630,426 A | 5/1997 | Eggers et al. | |
| 5,645,528 A | 7/1997 | Thome | 604/96 |
| 5,681,282 A | 10/1997 | Eggers et al. | 604/114 |
| 5,697,909 A | 12/1997 | Eggers et al. | 604/114 |
| 5,733,315 A | 3/1998 | Burdette et al. | 607/97 |
| 5,733,316 A | 3/1998 | Tierney et al. | 607/101 |
| 5,755,754 A | 5/1998 | Rudie et al. | 607/101 |
| 5,810,764 A | 9/1998 | Eggers et al. | 604/23 |
| 5,849,011 A | 12/1998 | Jones et al. | 606/47 |
| 5,891,134 A | 4/1999 | Goble et al. | 606/27 |
| 5,944,715 A | 8/1999 | Goble et al. | 606/41 |
| 6,171,306 B1 | 1/2001 | Swanson et al. | |

OTHER PUBLICATIONS

Dawkins, et al. "Radiofrequency heat–treatment to the prostate for bladder outlet obstruction associated with benign prostatic hyperplasia: a 4–year outcome study," *British Journal of Urology*, 79:910–914 (1997).

Djavan, et al. "Minimally Invasive Procedures and Medical Management—Their Relative Merits in Treating Lower Urinary Tract Symptoms of Benign Prostatic Hyperplasia", Reviews in Urology, 2:105–114 (2000).

Thermex Clinical Data, Direx Medical Systems, Nov. 1993.

Turapy Clinical Data, Direx Medical Systems, undated.

Brochure, SMK Sluijter–Mehta Kits, "The Finest Radiofrequency Electrodes for Pain Therapy" Radionics, Burlington, MA, 1996.

Blute, Michael L., et al., "Transurethral Microwave Thermotherapy for Management of Benign Prostatic Hyperplasia: Results of the United States Prostatron Cooperative Study," *Journal of Urology*; Nov., 1993; vol. 150, No. 5, Part 2 of 2; pp. 1591–1596.

Cosman et al., "Theoretical Aspects of Radiofrequency Lesions in the Dorsal Root Entry Zone" *Neurosurgery*, vol. 15, No. 6, 945–950, Dec. 1984.

Costello et al., "Nd:YAG Laser Ablation of the Prostate as a Treatment for Benign Prostatic Hypertrophy" *Lasers in Surgery and Medicine*, vol. 12, No. 2; pp. 121–124; 1992.

Goldberg et al., "Tissue Ablation with Radiofrequency: Effect of Probe Size, Gauge, Duration, and Temperature on Lesion Volume" *Acad. Radiol.*, vol. 2, No. 5 399–404, May 1995.

Goldberg, Nahum S., et al., "Hepatic Metastases: Percutaneous Radio–Frequency Ablation with Cooled–Tip Electrodes," *Radiology*; Nov., 1997; vol. 205, No. 2; pp. 367–373.

Goldwasser, B., et al., "Transurethral Needle Ablation (TUNA) of the Prostate Using Low–Level Radiofrequency Energy: An Animal Experimental Study," *European Urology*; Oct., 1993; vol. 24; pp. 400–405.

Harada et al., "Microwave Surgical Treatment of Diseases of Prostate" *Urology*, vol. XXVI, No. 6, 572–576, Dec. 1985.

Kramolowsky, et al, "The Urological Application of Electrosurgery," *The Journal of Urology*, vol. 146, 669–674, Sep. 1991.

Kramolowsky, et al, "Use of 5f Bipolar Electrosurgical Probe in Endoscopic Urological Procedures," *The Journal of Urology*, vol. 143, 275–277, Feb. 1990.

McGahan et al., "Percutaneous Ultrasound–Guided Radiofrequency Electrocautery Ablation of Prostate Tissue in Dogs" *Acad Radiol.*; vol. 2, No. 1; pp. 61–65, Jan. 1995.

Nardella, "Radio Frequency Energy and Impedance Feedback," *SPIE*, vol. 1068; pp. 42–48, (1989).

Onik et al., "Transrectal Ultrasound–Guided Percutaneous Radical Cryosurgical Ablation of the Prostate," *Cancer*; Aug. 15, 1993; vol. 72, No. 4; pp. 1291–1299.

*Radionics Neurosurgical Instruments*, Trigeminal Neralgia Kit Description, (1981).

Schulman, Claude C., et al., "Transurethral Needle Ablation (TUNA): Safety, Feasibility, and Tolerance of a New Office Procedure for Treatment of Benign Prostatic Hyperplasia," *European Urology*; vol. 24; pp. 415–423; 1993.

Sunshine, Robert D., M.D., et al., "Complications of Transurethral Resection of the Prostate," *Urologic Complications, Medical and Surgical, Adult and Pediatric*, 1986; Chapter 18; pp. 231–246.

Tucker, et al, "A Comparison of Urologic Application of Bipolar Versus Monopolar Five French Electrosurgical Probes," *The Journal of Urology*, vol. 141, 662–665, Mar., 1989.

* cited by examiner

PERI-URETHRAL ABLATION

CROSS-REFERENCE TO RELATED APPLICATIONS

This application is a continuation-in-part of application Ser. No. 09/021,802, filed on Feb. 11, 1998, now U.S. Pat. No. 6,440,127, entitled "METHOD AND SYSTEM FOR PERFORMING INTRA-URETHRAL RADIO-FREQUENCY URETHRAL ENLARGEMENT", and a continuation-in-part of application Ser. No. 09/113,683, filed on Jul. 10, 1998, now U.S. Pat. No. 6,447,505, entitled "BALLOON CATHETER FOR INTRA-URETHRAL RADIO-FREQUENCY URETHRAL ENLARGEMENT", and a continuation-in-part of application Ser. No. 09/287,589, filed on Apr. 6, 1999, now abandoned, entitled "THERMAL URETHRAL ABLATION."

FIELD OF THE INVENTION

This invention relates generally to advances in medical systems and procedures for prolonging or improving human life. More particularly, this invention relates to an improved method and system for alleviating urinary obstruction caused by enlargement of the prostate by performing thermal ablation for urethral enlargement.

BACKGROUND OF THE INVENTION

A majority of all males over 60 years old experience partial or complete urinary obstruction because of enlargement of the prostate. This condition usually originates from benign prostatic hyperplasia (BPH), which is an increase in cell mass near the urethra, or less likely, from prostate cancer. Both these conditions involve an increase in prostatic tissue mass, which in its increased state encroaches on the urethra and obstructs the urinary pathway.

In the case where urinary obstruction is caused by BPH, a common treatment involves a medical procedure using a medical side-cutting instrument and/or endoscope to surgically enlarge a passageway for urine flow through the prostate. The side-cutting instrument or an endoscope is passed through the penis into the urethra and is surgically used to remove prostate tissue and part of the urethra at the point of obstruction. This procedure is referred to as "Trans-urethral Resection of the Prostate" (or "TURP").

This procedure, although effective, is invasive and complicated. For example, it requires the use of anesthesia and substantial hospital care. It also has the risk of causing bleeding. Moreover, it is expensive and causes great discomfort and trauma to the patient. For example, chapter 18, entitled "Complications of Transurethral Resection of the Prostate," by R. Sunshine and M. Droller, of a book entitled *Urologic Complications, Medical and Surgical, Adult and Pediatric*, edited by Fray S. Marshall (Yearbook Medical Publishers, 1986), elaborates on the various complications of the TURP procedure.

In the case where urinary obstruction results from prostatic cancer, surgical prostatectomies are commonly used to eliminate the obstruction. However, surgical prostatectomies have serious side effects and risks, including impotence and urinary incontinence.

In recent years, less invasive systems and procedures that inflict less trauma on patients have been attempted. One such procedure, called "Trans-urethral Needle Ablation" (or TUNA), involves passing a radio-frequency (RF) instrument such as a catheter, cannula, sheath, or scope into the urethra. The RF instrument houses special RF electrode tips that emerge from the side of the instrument. The tips are pushed out of the instrument along off-axis paths to pierce the urethral wall and pass into the prostatic tissue outside of the urethra. As a result of the various electrodes emerging from the side of the instrument, such radio-frequency instruments are frequently complex and expensive.

By heating the prostate with RF power applied through the electrode tips emerging from the side of the radio-frequency (RF) instrument, the prostate tissue surrounding the urethra is ablated. Specifically, heat ablation is performed at multiple locations outside the urethra to provide a series of ablations, thereby causing the prostate tissue outside the urethra to die and necrose. Subsequent to heating, the necrotic tissue is absorbed by the body or excreted, thereby reducing the tissue mass outside the urethra, which consequently reduces the urethral obstruction.

For further explanation of this system and procedure, one can consult a research paper published by Goldwasser et al., entitled "Transurethral Needle Ablation (TUNA) of the Prostate Using Low-Level Radio-Frequency Energy: an Animal Experimental Study"; *Eur. Urol.*, vol. 24, pp. 400–405 (1993); and a research paper published by Schulman, et al., entitled "Transurethral Needle Ablation (TUNA); Safety, Feasibility, and Tolerance of a New Office Procedure for Treatment of Benign Prostate Hyperplasma;" *Eur. Urol.*, vol. 24, pp. 415–423 (1993). Also, product literature on the TUNA system available from a company named Vitamed, Inc., of Menlo Park, Calif., carries some description of the procedure.

The TUNA system and procedure is generally used to relieve urethral obstruction caused by BPH. It favors a transurethral approach because the target tissue to be ablated is generally near to it. However, again, although the TUNA system and procedure is effective, it requires epidural or general anesthetic, and generally causes the patient great discomfort and pain. Moreover, the TUNA procedure is medically and technically very complex for surgeons to perform, requiring a complicated and expensive catheter or sheath or RF electrode system to perform it. Also, it is a relatively blind procedure in the sense that the ends of the RF electrodes emerging at the side of the radio-frequency electrode system, once they penetrate the target tissue, cannot be seen. Nor is there any technique for providing a visual representation of them. Furthermore, the TUNA system and procedure attempts to leave the urethra intact and uninjured by the application of RF heating, which is difficult to achieve, making its outcome uncertain. The TUNA system and procedure causes scratching of the urethra, bleeding or irritation from a cystoscope, cannula, catheter, or tissue-piercing electrode tips passed into the urethra. Furthermore, the TUNA procedure produces trapped coagulated and necrotic tissue or fluid in the interstitial region of the prostate outside the urethra. This can result in swelling and increased pressure of tissue outside the prostate as the necrotic tissue is absorbed by the body. Such pressure can compress the urethra to further enhance its obstruction.

Another system and procedure contemplated by Onik et al. is described in their research paper entitled "A Transrectal Ultrasound-Guided Percutaneous Radical Cryosurgical Ablation of the Prostate," *Cancer*, vol. 72, pp. 1291–1299 (1993). This technique is utilized for the treatment of prostate cancer and involves disposing cryogenic (freezing) probes in the prostate for ablating the cancer cells. Onik et al. propose passing a cryogenic probe transperineally (through the perineum) into the prostate. At the same time, an imaging ultrasonic probe is passed through the rectum and is used to visualize the position of the cryogenic probe and the volume of cryogenic ablation in the prostate. This technique requires use of cryogenic probes (also referred to as cryo-probes) having relatively large diameters. The cryo-probes are complex in construction and operation and require elaborate cooling and thawing cycles, making the procedure typically quite complicated and expensive. It is technically challenging and critical to maintain precise temperatures at the target tissue area to prevent hemorrhaging when removing the probe and also to prevent freezing sensitive rectal mucosa tissue.

One more recent procedure contemplated and reported by McGahan, et al., in their research paper entitled "Percutaneous Ultrasound-Guided Radio-frequency Electrocautery Ablation of Prostate Tissue in Dogs," *Acad. Radiol.*, pp. 61–64 (1994), involves placing an RF electrode transrectally into the prostate of a dog under rectal ultrasound guidance. Their intent was solely to explore the feasibility of ablating cancerous tumors within the peripheral region of the prostate. Their research treated only normal animals and no ablation of cancer tissue was actually performed. McGahan et al. hoped to prevent RF heat ablation of the urethra (which is located centrally in the prostate). To achieve their objective, they suggested that the urethra should be irrigated with saline solution, using a catheter, to prevent RF heat damage to the urethra and periurethral tissue. They concluded that their system and procedure was impractical for ablating prostate cancer cells, because the RF lesions were limited to 1 to 1.5 cm in diameter, which they felt would be too small to adequately treat malignant cancer cells.

Generally, prostate cancer primarily occurs in the peripheral (non-central) zone of the prostate. It is often multi-focal, near the rectal wall, and near nerves controlling potency. Recognizing the restraints and delicate circumstances, McGahan et al., were discouraged by the results of their research. They concluded that their technique may be applicable to only a small percentage of prostate carcinomas, specifically those that are small and can be imaged by ultrasound. In their paper, they emphasized their concern for preventing RF heat damage to the rectal mucosa tissue. Thus, as a result of their efforts to treat prostate cancer, which is predominantly located in the peripheral non-central part of the prostate, they focused their research efforts on the peripheral, peri-rectal regions of the prostate. Their research did not contemplate RF ablation in the central periurethral region to produce an ablation cavity near the urethra or to ablate the urethra itself. In fact, they explicitly sought to avoid injury of the urethra by avoiding treatment of periurethral tissues. Their method and objectives were directed to cancer and were found to be disadvantageous for treatment of BPH or for treating urethral or periurethral tissues by radio-frequency (RF) ablation to relieve urinary obstruction.

It should be recognized that the theory behind and practice of RF heat lesion has been known for decades, and a wide range of RF generators and electrodes for accomplishing such practice exist. For example, equipment for performing heat lesions is available from Radionics, Inc., located in Burlington, Mass. Radio-frequency (RF) ablation is well known and described in medical and clinical literature. To that end, a research paper by E. R. Cosman, et al., entitled "Theoretical Aspects of Radio-frequency Lesions in the Dorsal Root Entry Zone," *Neurosurgery*, vol. 15; no. 6, pp. 945–950 (1984), describing various techniques associated with radio-frequency lesions, is incorporated herein by reference. Also, a research paper by S. N. Goldberg, et al., entitled "Tissue Ablation with Radio-frequency: Effect of Probe Size, Gauge, Duration, and Temperature on Lesion Volume," *Acad. Radiol.*, vol. 2; pp. 399–404 (1995), describes techniques and considerations relating to tissue ablation with radio-frequency energy.

In addition, a paper by S. N. Goldberg, et al., entitled "Hepatic Metastases: Percutaneous Radio-Frequency Ablation with Cooled-Tip Electrodes," *Radiology*, vol. 205, no.2, pp. 367–373 (1997), describes various techniques and considerations relating to tissue ablation with radio-frequency electrodes having cooled electrode tips. Cooled ablation electrodes will maintain tissue near the electrode at lowered temperatures which are below ablation temperatures. Cooling of the urethra by a catheter is suggested by McGahan et al., cited above, to prevent RF heat damage to the urethra and periurethral tissue.

Generally, cooled radio-frequency electrodes having an elongated shaft or catheter structure have cooling channels within the electrode structure. These cooling channels, for example, may comprise a first channel to carry cooled fluid from an external source, which is connected to the electrode at its proximal end. The coolant fluid is carried through the first channel to provide cooling to the electrode end, which is typically near the distal end of the electrode structure. The electrode structure typically also comprises a second channel within the electrode structure that is connected near the distal end to the first channel and which is adapted to bring the cooling fluid from the distal electrode region back to the source. Such recirculating channels for cooling fluid move the cooled fluid in one direction from the fluid source to the electrode and then back to the source. For a self-contained, internally cooled, electrode structure, the cooling channels would be inside the structure and sealed from other channels that may exist within the catheter such as for urinary drainage or for inflation of a balloon tip. Thus cooled electrode structures add a complexity of structure compared to non-cooled electrode structures.

Use of cooled ablation devices placed inside the urethra would have the objective of sparing the urethra from heat damage during the time when heating of prostatic tissue is occurring at a distance from the urethra.

Transurethral microwave thermotherapy (or "TUMT") has been used to treat BPH and illustrates the use of a cooled catheter which also delivers heat energy to the prostate. A catheter which has a microwave probe inside it is inserted into the urethra to the point of the prostate. The microwave probe is typically a microwave antenna which is located inside the catheter near its distal end and is connected to an external generator of microwave power output. In this way the prostate is heated by radiative electromagnetic heating. At the same time the catheter is cooled by circulation of a coolant fluid within the catheter. The objective is, as stated above, to cool the urethra and thereby prevent damage to it by the heating process which is occurring in prostatic tissue that is outside of and at a distance from the urethra. Thus, the TUMT procedure seeks to preserve the urethra and the prostate tissue immediately outside the urethra by cooling the catheter with fluid coolant that is circulated within the catheter. In TUMT, the microwave antenna is located inside the catheter and not in conductive electrical contact with the urethra. The microwave heating in the TUMT procedure occurs in the prostatic tissue located at a distance away from the urethra as a result of the simultaneous cooling action of the channels within the catheter and the deposition of microwave power into the prostate tissue from the radiated energy from the antenna. Thus the prostatic tissue immediately around the urethra and the urethra itself are deliberately spared from receiving an ablative level of heating in the TUMT procedure. Further explanation of the TUMT system and procedure can be found in the paper by Blute, et al., entitled "Transurethral Microwave Thermal Therapy for the Management of Benign Prostatic Hyperplasia: Results of the United States Prostration Cooperative Study," *J. Urol.*, vol. 150, pp. 1591–1596 (1993).

SUMMARY OF THE INVENTION

Conventional techniques such as those described above have not been directed at creating ablation of urethra or the periurethral region (the region surrounding the urethra or the critical prostate region) for the reasons discussed above. The present invention is based, in part, on the realization that it would be desirable to have an effective technique to perform intra-urethral ablation of the urethra and periurethral tissue for the purposes of alleviating urinary obstruction caused by enlargement of the prostate and that avoids the limitations of the art (e.g., piercing the urethra).

The present invention is directed to a system and procedure for heat ablation of prostatic tissue through the use of a thermal probe that is advanced into the urethra through the penis and positioned intra-urethrally (within the urethra). The ablation is performed for the treatment of benign prostatic hyperplasia (BPH) and the associated alleviation of urethral obstruction. It would also be used for other diseases such as prostate cancer to relieve urethral obstruction. The system and procedure of the present invention are different from any of the systems and procedures discussed in the background section. The advantages of the present system and method reside in their combined simplicity, economy, control, consistency, enablement of good ablation position and shape, and clinical effectiveness.

As one example, urinary bladder outlet obstruction can be effectively treated using the present system and technique, which is minimally invasive. The technique of the present invention involves inserting a thermal probe into the urethra to the region of urethral obstruction in the prostate. The thermal delivery portion of the probe remains within the urethra. This avoids the more difficult and uncomfortable transurethral approach of the TUNA system procedure discussed above, and may be done without need for passing one or more side-outlet RF electrodes through the urethral wall (via a transurethral approach) into the prostatic tissue surrounding the urethra. In various embodiments, the present system and procedure may include image guidance, which may be performed in a variety of ways including ultrasound, CT, MRI, fluoroscopy, X-rays, or other well known imaging techniques.

In accordance with one embodiment of the invention, a thermal probe may comprise a flexible rubber urethral catheter having an inflatable balloon tip and urinary drainage channel. A thermal heating element comprising a resistive heating element is attached to the catheter proximal to the balloon portion. This heating element can thermally contact the urethral tissue when the catheter is inserted through the penis into the urethra. The balloon may be inflated when the distal portion of the catheter is within the patient's bladder thereby enabling the catheter and the heating element to be fixed in a desired position relative to the prostate and urethra. The heating element may be determined to be at a desired position in the prostate by a simple traction of the balloon on the bladder. This also ensures against migration or change of position of the electrode from its proper position relative to the prostate and critical structures. X-ray, fluoroscopic, ultrasound, CT, or MRI imaging information can be made of the position of the electrode within the prostate and urethra.

In yet another embodiment of the invention, the thermal heating element of a urethral catheter comprises a flexible thermal element that can flex to conform to the curves of the urethra for insertion. The thermal element may comprise, for example, a resistive heating element, an RF conductive surface element, a conductive segment of the catheter, or an electrode or radiating element that is curvable and flexible for comfortable insertion into the urethra.

An electrical connection is made from the heating element to a power generator external to the patient's body. The output from the generator is used to heat and thus ablate the urethral tissue and surrounding prostatic tissue near the heating element location. This creates a cavity and expanded opening of the urethra to relieve the urinary obstruction caused by BPH or other prostatic disease.

In contrast to the TUNA technique, the thermal probe of the present invention can be used without piercing the urethra. It enables patients who cannot tolerate the TUNA system and procedure to receive urethral ablation treatment. For example, such patients could be those requiring anticoagulation medication for cardiac or neurological problems who should not risk bleeding from a punctured urethra.

In a technique performed according to the present invention, a thermal probe is made to ablate a portion of the urethra and the periurethral region (i.e., tissue near or on the urethral tube) to induce necrosis of the prostate tissue near the urethra and of the urethra itself. This induces a cavity to be formed via obliteration of a portion of the urethra and the central region of the prostate in the patient's body a few days after the procedure is performed. The cavity provides direct communication to and widening of the urethral channel. In accordance with one embodiment of the invention, thermal ablation depths of several millimeters into the periurethral tissue can be made, which thereafter induce similar sized cavities to be formed, thereby enlarging the urethral passage. These exemplary lesion sizes, similar to those made by the TURP procedure, have proven to be adequate to provide relief from BPH.

It should be noted that in contrast to McGahan et al.'s conclusion that RF lesion sizes are inadequate for the ablation of prostate carcinomas, the periurethral ablation sizes are adequate in treating BPH. Periurethral ablation in accordance with the present invention may also be used to ablate cancerous tumors of the prostate that may be located in the region of the urethra.

Also, the present technique avoids the need to observe McGahan et al.'s admonition to avoid heat or thermal injury of the urethra, and corresponding necessity for the irrigation and cooling of the urethra as suggested by the article by McGahan et al. By ablating the urethra itself, the present technique has the added advantage of avoiding the possibility of necrotic tissue and liquid becoming entrapped outside the urethra if the urethra is left intact, as in the case of the TUNA and McGahan et al. procedures.

The system and procedure of the present invention differs from TUMT techniques which seek to preserve the urethra by fluid cooling within the electrode catheter. The present technique seeks to ablate a portion of the urethra and periurethral tissue and so directly widen the urethral channel. The present technique has the advantage over the TUMT technique of not requiring added coolant-carrying channels within the catheter which increase complexity and cost of the TUMT electrode systems. The electrodes of the present invention are also simpler than the TUMT devices. The present invention involves a simply constructed thermal probe that is in thermal contact with or in physical contact with the urethra as compared to an internally located and complex microwave antenna structure in the case of the TUMT device.

The system and method of the present invention has the further advantage of increased simplicity, safety, and economy. The probe structure may be of a simple construction and geometry in one form not requiring coolant channels (although other versions can be made with cooling channels). This has the advantage that the catheter and thermal probe are easy to construct and therefore economical. The probe can be inserted easily by any urologist or clinical assistant. Also, it is well tolerated by patients, even those who are in frail health. The systems and methods of the invention are safe. For example, the simple use of the embodiment of an inflatable balloon within the urethra combined with catheter traction and X-ray imaging with contrast injection assures the correct positioning of the thermal probe within the urethra and prostate.

These features and advantages as well as others of the present method and system will become apparent in the detailed description that follows.

BRIEF DESCRIPTION OF THE DRAWINGS

In the drawings, which constitute a part of the specification, embodiments exhibiting various forms and features hereof are set forth, specifically.

DETAILED DESCRIPTION OF THE INVENTION

Figure 1:
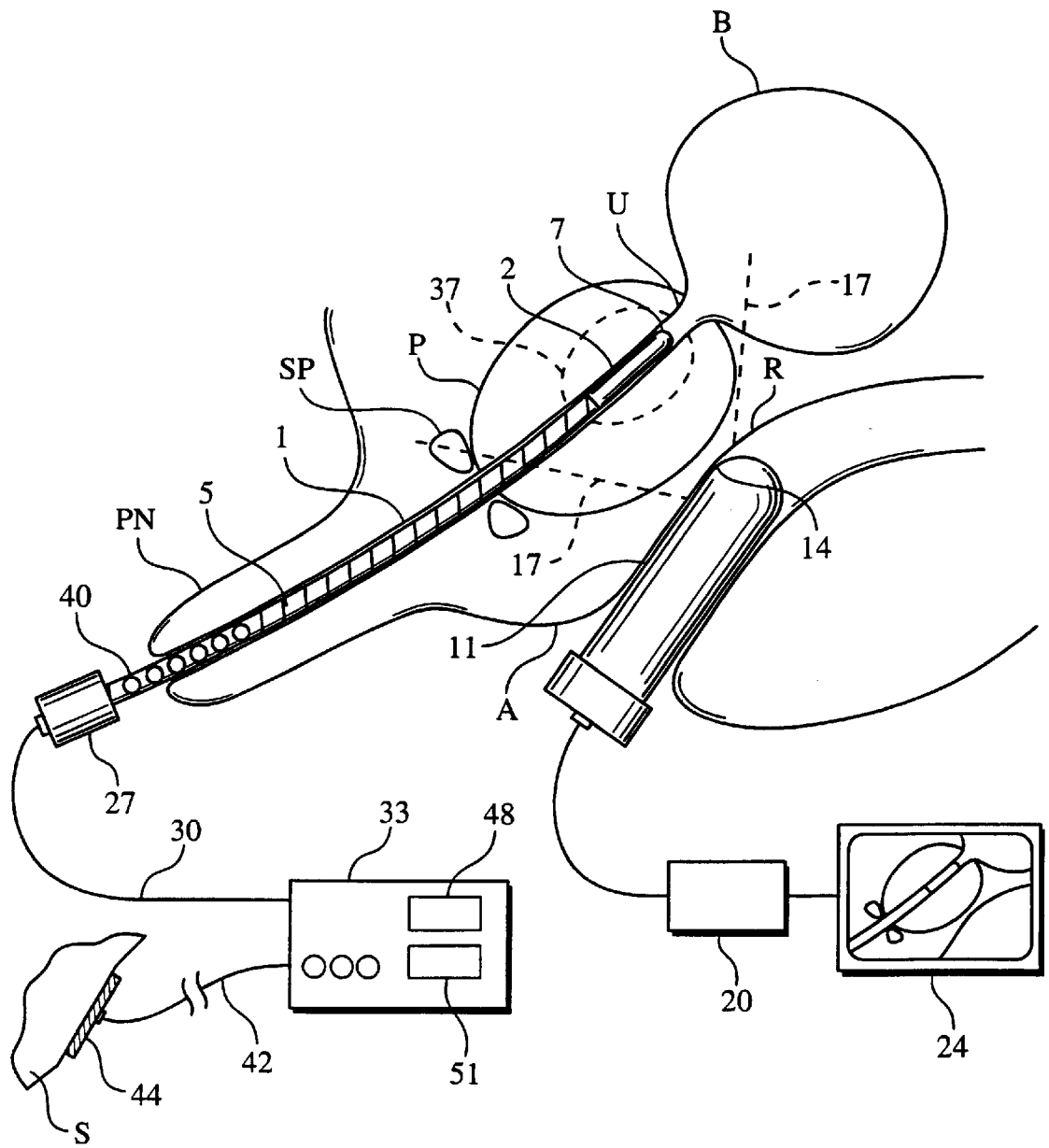
FIG. 1 is a schematic diagram showing a portion of a patient along with a system according to the invention for performing intraurethral thermal ablation of the urethra and central prostate with ultrasonic imaging guidance.

Referring initially to FIG. 1, in a system in accordance with the present invention, a probe 1 is inserted via the penis PN into the urethra U of a living body, such as a patient, and into an operative field within the patient's body, specifically including the prostate gland P. The tip 2 of the probe 1, which is a thermal element, is placed intraurethrally, within the urethral tube that drains urine from the bladder B in the living body. In the disclosed embodiment of the invention, the probe 1 has an insulated shaft portion 5, indicated by the hatched area in FIG. 1. The probe tip 2 preferably has a rounded distal end 7 to facilitate passage through the urethra and into the prostate region without scraping, cutting, or penetrating the urethral wall itself. This configuration of the probe 1 facilitates the intraurethral approach to placing a thermal element into the prostate.

Also shown in FIG. 1 is an ultrasonic imaging device 11 which is placed intrarectally through the anal opening A. It has an imaging head 14 which rests against the rectal wall R near the prostate P. The ultrasonic imaging device 11 may be any common tool used in diagnostic medicine; such devices are widely available. For example, Accuson, Inc., located in Mountain View, Calif., provides several suitable ultrasonic imaging devices. With the ultrasonic imaging device 11, any desired area of tissue may be imaged. In one embodiment of the invention, the imaging head 14 comprises an ultrasonic scanning transducer.

For example, as illustrated in FIG. 1, the region of tissue falling within the area bounded by the dashed lines 17 is scanned by the ultrasonic scanning transducer 14 to generate a visual image. This image may include the rectal wall R, prostate P, and urethra U, as well as the electrode 1 and its thermal probe tip 2. The ultrasonic scanning transducer 14 is connected to an ultrasonic image processing unit 20 and a display unit 24, as is common practice. The display unit 24 serves to provide real-time ultrasonic images of the prostate P with the tip 2 placed in the urethra U. This way, the guidance provided by the ultrasonic image is used to locate the thermal element 2 at an appropriate point of the urethra within the prostate and, if desired, away from particularly sensitive areas such as the apex of the prostate near the sphincter SP.

The probe 1 has a connection 27 at its proximal end (nearest the surgeon), which is connected by a wire or cable connection 30 to a generator or other energy source 33. The generator 33 may be a source of electrical voltage or current which connects through cable 30 to a resistive heating element in tip 2 that in turn causes thermal ablation of the urethra near the tip 2. In one embodiment, generator 35 may be a laser energy source that delivers laser power through 33 to a laser emitting tip 2 to heat ablate the urethra near it. In other embodiments, the generator may be an electrical unit with, for example, a radio-frequency, microwave, or other high frequency power supply that can deliver a high-frequency electrical signal to a conductive electrode tip 2.

Probe tip 2 can include a resistive wire element or heater element that heats up when electrical current passes through it. The current can be generated by generator 33 and passes through two current conductors inside connection 30 to/from the resistive heater element in tip 2. The heat so generated will spread to the urethral and peri-urethral tissue nearby causing tissue ablation in an ablation zone indicated by the dashed line 37. The resistive heater elements or wires may be constructed using known technology and, for example, could include the use of a high resistance wire such as nichrome wire inside tip 2 connected to lower resistance wires such as copper wires inside catheter 1 which connect to the connection cable 30. The nichrome wire will heat up by ohmic heat dissipation in the thermal element tip 2. Very little heat will be generated in the connection wires leading to current generator 33, keeping all but the tip 2 from rising above ablation temperatures.

Alternatively, in accordance with known technology, generator 33 can be a laser power source, and cable 30 can carry laser light through probe 5 to a diffuser or transmitter element in tip 2. Thereby, the laser light power can be sent out of tip 2 into surrounding tissue causing heating and ablation of the urethra and prostatic tissue in an ablation zone schematically illustrated by dashed line 2.

In another embodiment, in accordance with known technology for generating radio-frequency (RF) lesions, as described in the Cosman and Goldberg articles described above, a high-frequency signal applied to the exposed tip 2 generates a heated region around the tip 2, which in turn produces a heat lesion or ablation zone 37 around the exposed tip 2. The size of the ablation zone or heat lesion 37 may be increased by increasing the power from the energy source 33 that is applied to the tissue. Thus, the size or volume of the ablation zone 37 can be graded and controlled around the urethral channel.

Also shown in FIG. 1 is a second cable 42 that may be placed in conductive contact with a portion of the patient's skin S or other part of the body via a second electrode 44. The second electrode 44 serves, as is common practice, as a reference or return electrode for the RF current emitted from the RF electrode tip 2. Examples of RF lesion generators and RF electrodes using this configuration can be found in the product literature of Radionics, Inc., Burlington, Mass.

The generator or energy source 33 may have temperature meters 48 or other ablation parameter readouts 51, illustrated by a digital meter reading, for display of power, current, voltage, impedance, or other parameters associated with the heating process.

To give a specific illustration of how urinary blockage is reduced in accordance with the system of FIG. 1, probe 1 with, for example, a diameter of 2 mm is partially covered with an insulating coating 5 (the hatched area). A conductive portion 2 is fabricated from a conductive metal tube, such as stainless steel. For MRI compatibility, other materials with low magnetic susceptibility (such as high cobalt nickel content materials, e.g. Inconel or copper) may be used so that direct MRI imaging of the lesion process and electrode positioning can be done.

In the disclosed embodiment, the tip 2 may have a length of approximately 5 to 20 mm. The tip may have a hemispherical, rounded point on its distal end 7 to prevent abrasion or penetration of the urethra U. The electrode may be self-contained or sealed. Alternatively, it may be a flexible catheter-type electrode wherein the insulating coating 5 is a plastic, urethane, polyethylene, silicone, or other material. In this case, the tip may be a conductive metal tip which is fused to the flexible catheter structure 5. Within the catheter may be electrical wires which connect to the thermal element tip 2 and are brought out to make connection with the external cable 30 through a hub 27.

In accordance with another embodiment of the invention, the electrode 1 may have an outer cannula, as in a needle, with an inner obdurating stylet to facilitate insertion. Once inserted into the urethra as in FIG. 1, the stylet may be removed and other structures inserted in its place, such as fiber optic endoscopic visualization probes, temperature sensing probes, multiple temperature-sensing probes, and so on. The electrode tip in any of these configurations may also include a temperature sensor built into the tip, or alternatively the system may include a temperature-monitoring probe that is inserted into the catheter or cannula once the instrument is in place within the urethra.

By carefully placing the probe in accordance with FIG. 1 within the catheter and positioning the tip 2 in an appropriate portion of the urethra U where there is a urinary obstruction, an effective ablation of the prostate can be accomplished. By supplying power from the energy source 33 to the tip 2, heating of the urethra adjacent to the tip 2 and the surrounding periurethral tissue in the vicinity of the tip will occur. In accordance with one embodiment, a heat lesion of desired size is formed by controlling the temperature of the heated urethra and prostate tissue immediately surrounding the tip 2 to approximately 90° C. At this temperature, an ablation volume will be formed having a diameter of several millimeters. This ablation volume will engulf the urethra and the periurethral tissue and be entirely contiguous with the remaining urethra connected to it. The size of the heat lesion is visualizable on CT or MRI image scanning at the same time or after the lesion is made.

In accordance with other embodiments, depending on the lesion sizes desired, other tip temperatures or prostate tissue temperatures ranging between 50 and 100° C. are used. The desired lesion sizes are determined (for example 0.3 to 5.0 cm) depending on the size and geometry of the patient's prostate or urethral obstruction or other clinical considerations.

The energy source 33 has a power range from 0 to approximately 50 watts, although 20 watts or less is generally adequate to achieve the temperatures cited above. The electrode tip 2 has a temperature sensor built inside the tip or on its surface, which may be a thermistor, thermocouple, or other type of temperature sensor. The temperature sensor is connected via connection wires extending inside the shaft 1 to the energy source 33 including its meter 48, thereby enabling temperature monitoring by the clinician. The measured temperature at the tip is representative of the temperature of the urethra and the nearby prostate tissue as the ablation proceeds.

The shaft of the probe 1, in accordance with one embodiment of the invention, is approximately 20 to 30 cm in length. In other embodiments, lengths up to 60 cm may be used. It should be recognized that varying sizes, geometries, probe tip configurations, tip diameters and lengths, etc. may be used for the probe 1 to produce heat lesions.

The ultrasonic imaging device 11, which in one embodiment of the invention is the EPOXP Monitor available from Accuson company, Mountain View, Calif., is used to provide images on the display screen 24. The ultrasonic image on the display may show the shaft 1 and the tip as they are positioned within the prostate, and this is visualized on the screen display 24. The surface of the tip 2 or the shaft 1 may be roughened, scored, or otherwise configured to make it more visible via ultrasonic imaging.

The depth of penetration of the probe 1 and its tip 2 within the prostate and urethra may be gauged by scale or indicating markings 40 on the shaft of the electrode 1 near its proximal end. If different positions of the tip need to be implemented, the depth of insertion of the probe in the penis and urethra can be changed according to the scale markings 40. For example, the ultrasonic image display 24 may indicate that the tip 2 is too deep or too shallow within the urethral tract inside the prostate. Accordingly, the shaft may be moved in or out quantitatively by the scale markings 40.

Figure 2:
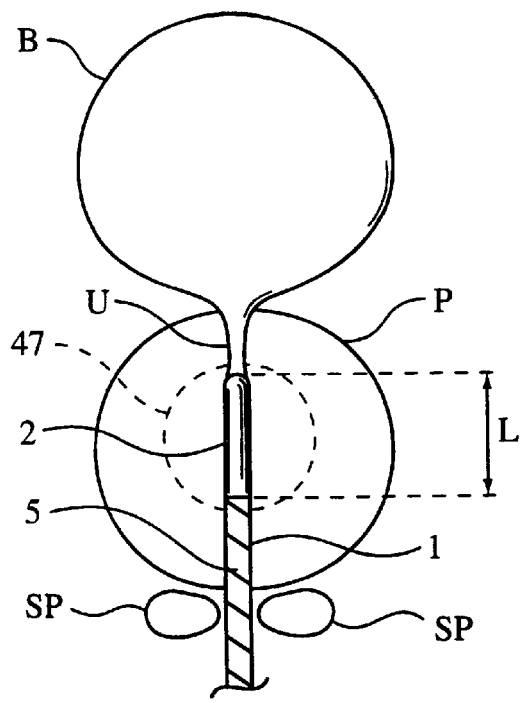
FIG. 2 illustrates a procedure or technique by which thermal probe is located intraurethrally near a point of urethral obstruction in the prostate to make a urethral ablation.

FIG. 2 shows a diagram illustrating the manner in which a thermal lesion is made by a thermal probe placed intraurethrally. Generally, a patient's bladder B is illustrated; it is in fluid communication with the patient's urethra U. The probe 1 is inserted into the urethra U, as shown, to place the tip 2 within the urethra near a point of urethral obstruction. As above, the shaft of the probe 1 has an insulated portion 5 (the hatched area). When energy is delivered from the energy source 33, as in FIG. 1, dissipation of the energy around the tip 2 causes a heating zone to occur around the tip. This will cause a zone of heat ablation 47, which engulfs the urethra U and the periurethral tissue within the dashed line volume. The zone 47 indicated by the dashed line would, for example, illustrate a typical isotherm surface area or area of constant temperature within which all tissue is raised to a lethal or ablation temperature. An example of a desired temperature for ablation to kill prostate tissue is approximately 50° C. maintained for six minutes. It should be recognized that variations, depending on the desired outcome, are possible.

An ablation isotherm surface, therefore, is an indication of the region in which the cells are dead. At 50° C. or higher temperatures, tissue necrosis in the isotherms within the volume encompassed by the isotherm surface area is induced. Liquefaction of the necrotic tissue occurs within days from the day of treatment. If such an ablation isotherm area (corresponding to ablation or necrosis), as illustrated by the dashed line 47, engulfs the urethra in the region where there is a urethral restriction, then in a matter of days after treatment, the entire periurethral zone, including the urethra within the isotherm surface area, is obliterated and liquefied. The flow of urine from the bladder through the urethra will then carry away the liquefaction and debris from the necrotic tissue away and out of the body through the urethra.

Figure 3:
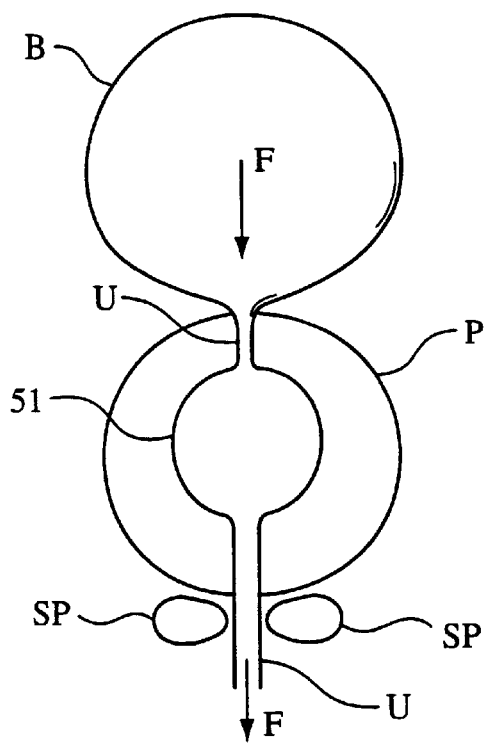
FIG. 3 illustrates a cavity in the prostate contiguous with the urethra induced by a system and method according to the present invention.

FIG. 3 illustrates the effects induced by the system and method for urethral enlargement by thermal ablation according to the present invention. The inventive system and procedure obliterates the urethra and region within the ablation isotherm surface boundary to induce a cavity 51. The urethra and prostatic tissue that previously was within this cavity volume has been necrosed and liquefied and passed out through the urethra U by the flow of urine, indicated by the arrows F, from the bladder B out through the penis PN (FIG. 1). The urethral wall has been obliterated to open the channel in communication with the remaining segments of the urethra. The cavity 51 is generally symmetric about the urethra to open a lumenal volume, thereby reducing the restriction of flow that previously existed with the urethral obstruction. Because the cavity 51 is located around the urethra, it is typically axially central to the prostatic gland. There is the advantage that the cavity has a smooth, contiguous continuity with the urethral structures connected to it, increasing the likelihood of laminar fluid flow after the cavity 51 has been formed. Since it is in the periurethral region, the inventive technique also has the advantage that it is remote from various critical structures such as nerves in the outer prostate and the rectal wall.

By way of further explanation, the urethral wall and the periurethral tissue that is in the area of the zone of necrosis is liquefied and carried away by urine flow F. As the urethral cross-sectional area is increased, the impedance to flow of the urine is substantially reduced and the flow vector F is increased in magnitude, restoring normal voiding function or improving voiding rate. The body reacts to this procedure by creating a new epithelial layer of cells, within a matter of a few weeks, to cover the interior surface of the cavity 51.

Because a typical isotherm surface area 47 (FIG. 2) is created in a generally central area of the prostate because of the intraurethral location of the thermal tip, the peripheral annulus of the prostate acts as a natural margin of safety or thermal buffer zone for the critical organs, which typically lie outside the peripheral region or just outside the prostate. These would include critical nervous structures and the rectum wall and mucosa.

During the process of carefully positioning the tip 2 relative to the urethral obstruction and the prostate (as illustrated in FIG. 2), a visualization representation is relayed via the ultrasonic detector or imaging head 14 and displayed on the ultrasonic display 24 (FIG. 1). This allows the tip 2 to be safely guided and located in the proper region of the prostate and away from delicate regions such as the sphincter SP.

The length L of the exposed tip 2 may vary or be chosen according to the length of the ablative isotherm volume 47 required. For a fixed length L, the position of the tip 2 may be translated after a first lesion to another position within the prostate to enlarge the length of the cavity 51 (FIG. 3). Thus, multiple thermal ablation stages may be considered according to clinical needs to enlarge the length of the urethral cavity enhancement.

In accordance with another embodiment of the present invention, the probe may not include the temperature sensor. The correlation of an ablation size desired to a certain electrode tip geometry may be determined by considering generator parameters such as power output, voltage, and current. Generally, it can be determined that ablation temperatures of greater than 50° C. in the prostate tissue can be induced, for example, by way of power or current levels greater than known amounts. This information can be used by clinicians to induce sufficient ablation sizes to alleviate urinary obstructions by the intraurethral method, depending on clinical circumstances.

In certain embodiments of the invention, the probe itself is self-contained, having a unitized metal shaft such as a tube of stainless steel or other material with an enclosed, sealed tip. Inside the tip 2 is a thermocouple, thermistor, or other temperature sensor. The sensor may be in the interior of the tip or integral with the surface of the tip. The electrode shaft may be electrically insulated by any of various suitable materials, sheaths, or coating, such as epoxy, Teflon, etc. The hub 27 of the electrode 1 (FIG. 1) may be tubular or otherwise shaped to best conform to the operator's fingers as he inserts it intraurethrally.

As described previously, the shaft of the probe 1 or the tip 2 may have properties to optimize visualization. For example, a roughened surface on the tip 2 can make it more exogenic and visible in ultrasonic imaging. Furthermore, a metal tip may be visible in an X-ray image to locate the position of the tip in the prostate during the procedure. Alternatively, the probe may be made of MRI or CT compatible material so that it is visible in MRI or CT imaging without substantial artifacts. These imaging techniques may be used prior, during, or after the procedure to monitor the placement of the electrode and the progress of the necrotic periurethral cavity after ablation.

In accordance with another embodiment of the invention, the probe 1 as shown in FIG. 1 has an insulated shaft made of a flexible material such as plastic, silicone, polyurethane, etc. It may be similar to a catheter with a hollow interior to enclose the electrical connection or temperature sensing wires. The tip is made of metal and is bonded or connected to the flexible insulated shaft portion 5 by bonding agents, glue, swaging, or other means. A flexible catheter-like electrode has the advantage of being placed into the urethra U with greater ease and comfort to the patient.

Figure 4:
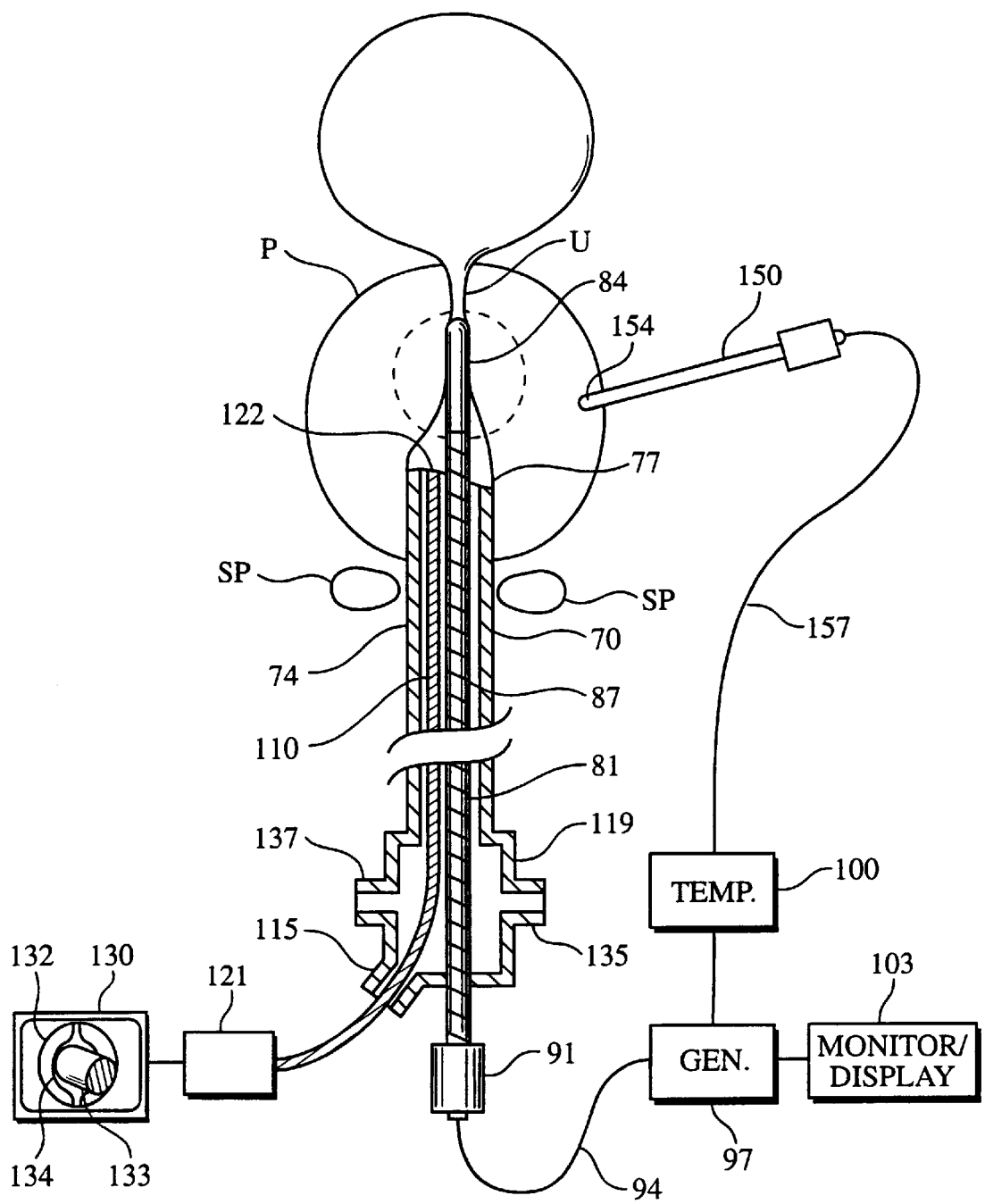
FIG. 4 shows another embodiment of a prostate ablation probe in combination with an endoscope passed into the urethra in accordance with the present invention.

FIG. 4 illustrates another embodiment in accordance with the present invention. An endoscope 70 is illustrated in sectional view, and has a cannula 74 which is inserted into the urethra, which is common practice for urologists. The endoscope 70 has a tip end 77 that is inserted past the sphincter and into the prostate region P. A probe 81 is then inserted through the endoscope cannula 74. It has a thermal tip 84 that extends beyond the endoscope tip 77 and remains within the urethra U. As in the previously described embodiment, the shaft of the probe 81 has an insulated surface portion 87 (hatched lines). The probe 81 further has a hub 91, facilitating connection via a connecting cable 94 to a generator 97, serving as a source of power output. A temperature-sensing readout 100 is used to read the temperature of the temperature sensor which is located within the tip 84 or by multiple temperature sensors located at other points along the electrode shaft 81. Readout of output parameters from the generator 97 can be accomplished by a monitor and display system 103, which in various embodiments may involve computers, controls, feedback systems, electronics, and even computer graphic displays to illustrate the parameters by a computer graphic workstation during the progress of the ablation.

Also shown in FIG. 4 is an optical visualization system which can be used in conjunction with the endoscope 70 and probe 81 in accordance with the present invention. An optical visualization element 110 is shown passed through the cannula 74. In the disclosed embodiment, this element 110 is a fiber optic channel inserted through a port 115 on a hub 119 of the endoscope 70. A fiber optic control unit 121 processes the signal from the fiber optic channel 110, and also may control illumination sources that can provide illumination down the fiber optic channel into the region of the prostate near the tip 84. A processing display unit 130 can display an image field 132 as seen by the fiber optic channel 110 near the tip 84. The display is capable of showing an image 133 of the RF electrode 81 with respect to an image 134 of the urethra. Accordingly, at the tip 122 of the fiber optic line channel, a view of the region in the prostate where the ablation will take place can be displayed on the display 130. The position of the tip 84 within the urethra U can be visualized prior, during, and after heating. In this way, control of the position of the probe tip within the urethra can be accomplished under direct visualization, increasing the safety and certainty of the intraurethral technique.

By way of explanation, the use of cystoscopes or endoscopes in the urethra is common practice by urologists. A common cystoscope in use is the Urethroscope made by the Karl Storz company of Tuttlingen, Germany. Such devices commonly have fiber optic channels and imaging systems such as those illustrated in the description of FIG. 4, above. They also may have optional irrigation ports 135 and aspiration ports 137, also illustrated in FIG. 4. Because the tip 84 of the present system and method, as illustrated in FIG. 4, is under direct visual control by the endoscope fiber optic apparatus and display 130, better control and certainty of the placement of the tip within the urethra and prostate is provided. This is an advantage over the TUNA procedure, in which side-outlet radio-frequency electrode probes puncture the urethra and are therefore out of view of endoscopic fiber optic visualization.

Also referring to FIG. 4 and in accordance with the present invention, other temperature sensors may be placed in the prostate or nearby organs to monitor the process of the intraurethral ablation. For example, a temperature-sensing probe 150 may be placed within the prostate, for example, through the rectal wall. It has a temperature-sensing tip 154 which measures the temperature in the peripheral region of the prostate P. A connection cable 157 connected to the temperature sensor 154 passes a signal representative of the temperature to the temperature-sensing readout 100 in connection with the generator 97 and the control apparatus 103. Multiple satellite temperature-monitoring sensors may accordingly be present to qualify the thermal distribution, particularly in regions of organs at risk.

Figure 5:
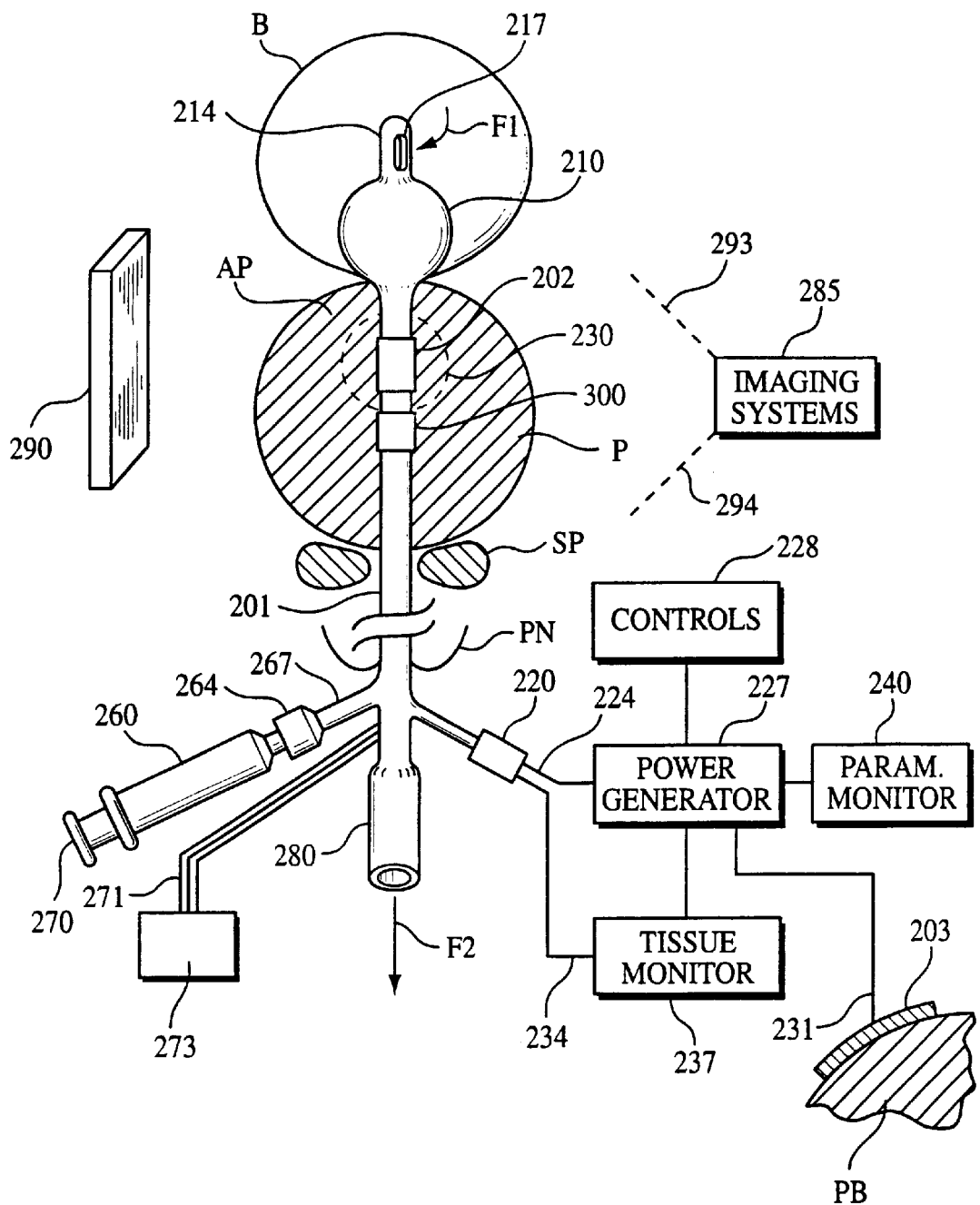
FIG. 5 shows another embodiment of a prostate ablation electrode integrated with a balloon catheter with multiple temperature sensors in accordance with the present invention.

FIG. 5 shows yet another embodiment of the system and procedure according to the present invention involving a catheter 201, which is passed into the urethra through the penis PN, which is shown only in partial sectional view. The catheter 201 has a thermal element 202, which is positioned in prostate P according to clinical needs to alleviate urethral obstruction. At the distal end of the catheter, there is an inflatable balloon structure 210 shown in an inflated state. There is further a distal tip 214 which defines an opening 217. Urine within bladder B can flow according to an arrow F1 into the opening 217 and out of a proximal end of the catheter, as illustrated by an arrow F2.

Rubber catheters with balloon ends are used commonly by urologists. Examples of such catheters are SILASTIC Foley catheters distributed by the Bard Urological Division of Covington, Ga. FIG. 5 shows an embodiment of the present invention in which such a catheter is augmented by a heat element or thermal element (structure 202) that may be formed in the shape of a ring. In the disclosed embodiment, the structure 202 is connected internally through the catheter 201 to a hub portion 220, a connection cable 224, and a generator 227. The generator 227 supplies a power output, as described in connection with the previous examples, to or through structure 202, resulting in heating of the urethral tissue to give rise to an ablation isotherm surface 230 (the dashed line). Temperature sensors may be located at multiple points along the catheter 201 within the prostate, and temperature signals carried by a connection 234 to a tissue temperature monitor 237 to monitor the ablation process as described previously. Additionally, monitoring of output parameters from the generator 227 may be accomplished via a parameter monitor 240.

The system in accordance with the present invention, illustrated in FIG. 5, may be implemented by the following illustrated example. The catheter 201 is sterile and disposable; it includes a power delivery structure 202 with hub or connection structures 220, as described above. The catheter 201 is inserted into the penis PN according to common practice until the balloon structure 210 is within the bladder B. The balloon is then inflated by a syringe 260 attached to an inflation hub 264, which is standard on Foley balloon catheters. Inflation by the syringe plunger 270 injects air or fluid into the balloon 210, thereby inflating the balloon and retaining it within the bladder B. If fluid is injected to fill the balloon, the fluid may be contrast fluid that is visible on X-ray or fluoroscopic images of the patient's body to confirm the balloon's position.

Once the balloon catheter is so entrapped within the bladder B by the inflation of the balloon 210, urine within the bladder B can flow according to the arrow F1 through the distal tip opening 217, and drain from a main catheter hub 280, as illustrated by the arrow F2. Once this configuration is established, an X-ray contrast medium may be injected through the hub 280 into the bladder B. An imaging system 285 such as a fluoroscope or X-ray machine can then be used to image the catheter tip 214, the balloon 210, the bladder B, and the heat element structure 202 together. An X-ray imaging detector 290 is shown which can collect X-ray images from X-rays emitted from, for example, an imaging system 285, as illustrated, within the field of imaging illustrated by dashed lines 293 and 294. Such X-ray images visualize and assure that the structure 202 is properly placed with respect to the bladder B and the prostate P. The imaging system will help ensure that the structure 202 is within the prostate at the point of urethral obstruction and sufficiently away from the apex of the prostate or the sphincter SP, which are critical structures.

The embodiment of FIG. 5 shows the structure 202 in an intraurethral position. As with the previously described embodiments, the heat ablation associated with the structure 202 will obliterate and necrose the urethra and periurethral prostatic tissue proximate to the structure 202. Also shown on the catheter 201 is a second element 300, which in various embodiments can be a second heat applicator element or thermal element structure or a temperature sensor. For example, if the region of ablation 230 (the dashed line) needs to extended to include a region around the electrode 300, then the output from the generator 227 could be applied to or through the electrode 300. This illustrates that multiple heating or power delivery elements can be placed on the same catheter structure 201 to grade the size of the ablation according to clinical needs.

In one embodiment, element 202 can be an exposed conductive ring that is connected to a radio frequency (RF) generator 227 by electrical connection wires 224 or 234. This will cause urethral ablation by RF tissue heating. Element 203 is a reference RF electrode connected to the generator 227 by cable 231. Element 300 may be another exposed conductive ring which could also be connected to the RF output of generator 227 to enlarge the size of the ablation. Electrodes 202 and 300 could be connected in a bipolar fashion to generator 227 which would cause the RF current to flow between them and eliminate the need for a grounding pad or reference electrode as illustrated by element 203 in FIG. 5. The bipolar electrode configuration would tend to create RF heating between the electrodes 202 and 300; by reference, see the references on RF lesion making cited above.

The element 202 may be a metal annular ring. The ring may be comprised of a sheet of solid metal wrapped in an annular structure to encircle the catheter 201. This structure may completely or partially encircle or segmentally encircle the catheter 201.

The annular ring may be solid in the sense of not being hollow or not having cavities within it. That is, the element 202 may be "cavity-free." The ring wall may vary in thickness from 0.001 millimeters or less to 1 millimeter or more. The ring may have a length ranging from 0.1 millimeters or less to several millimeters or even centimeters.

Element 202 may take many forms. Element 202 may comprise a non-fluid-containing electrode and/or a non-hollow conductive structure. For example, there may be no internal cavities in element 202, and it might not be connected to a fluid channel within the catheter. Alternatively, thermal element 202 may be a composite of solid metal wires or conductive plastic or composite material.

Element 202 may be flexible so that it can bend with the flexible catheter through the curves of the urethral channel; thereby providing improved patient comfort and minimizing harm to the urethra during insertion. The urethra has a major natural curve and the flexibility of the catheter and thermal element is a significant advantage to prevent patient discomfort or injury and to facilitate catheter insertion.

Element 202 may, in one embodiment, be a composite of solid conductive wires. For example, it may comprise a helix of conductive wires having either a tight wound or an open loose wound configuration. Element 202 may be a braided network of solid wires to form a mesh or surface braid that is on the surface of rubber catheter 201 or otherwise attached to it with anchoring structures within the catheter such as internal loops of a braid or waffles of a helix or wire structure to secure strongly in the proper position on catheter 201. Such structures may be flexible for the advantages cited above.

In another embodiment, element 202 may be a resistive heating element and thus a source of heat that spreads to the urethra and peri-urethral tissue by thermal conduction in the tissue. The analogy could be made to a soldering iron that heats up when current is passed through it. Element 202 could be a helical coil or resistive wire, such as nichrome or tungsten wire, which has a high resistivity and is well suited as a resistive heating element. The resistive wire could be wound in a tight or an open helix around a plastic or rubber catheter body 201. The helix could have a length of several millimeters or centimeters and diameter of several millimeters, depending on clinical needs. The resistive wire may be part of ring or braided structure bonded to the surface of or embedded into the wall of catheter 201. This structure may be of a flexible construction to bend with the catheter as it is inserted through the curved path of the urethra upon insertion; thereby providing the structural and clinical advantages of safety and functionality cited above.

Alternatively, if the structure 300 contains temperature sensors, then the tissue monitor 237 can read out tissue temperature near the structure 300 as an indication of ablation size. For example, if the temperature sensor in 300 reads less than 50° C., then this would indicate that the ablation zone 230 has not reached into the region near the structure 300.

In the exemplary embodiment of FIG. 5, the catheter 201 is made from SILASTIC rubber, as manufactured by Dow Corning, of Minneapolis, Minn. Its diameter is approximately 3 to 8 mm, and its length is in the range of 30 to 40 cm. However, other smaller or larger dimensions may suit varying clinical needs. The electrode structures 202 and 300 consist of stainless steel rings that are bonded to the SILASTIC substrate or the surface of the catheter 201.

Depending on the particular application, the electrode structures 202 and 300 may be non-cooled, non-fluid containing, non-hollow, non-cavity containing rings, ring segments, plates, wires, films, or sheets. They may be flexible or non-flexible. They may be non-metallic conductive elements. The electrode structures 202 and 300 may be made from wire structures or braids or conductive film, or flexible platings or flexible structures on the surface of the catheter 301 or embedded within the walls of the catheter. The electrode structures 202 and 300 may be rubberized flexible structures imbedded with conductive particulate matter such as carbon, metal, or other conductive agents, or helixes of wire or sheets. Other materials or platings may also be used, including but not limited to Inconel, titanium, or copper plated with gold, to suit various clinical needs. The balloon structure and body of the catheter could be similar to the Foley catheter mentioned above with an inflatable balloon 210, straight or curved distal tip 214, port 217, an injection port 264, and a main catheter urinary hub 280. In addition, the hub or other connection 220 for the resistive heating, laser, high frequency, or thermal monitoring cabling can be adapted to suit clinical needs. Internal connection wires within the body of the catheter 201 connect to the structures 202 and 300, as well as temperature sensors within the catheter at various points inside or extending outside the catheter walls.

A urological heat ablation catheter, as in FIG. 5, is easily inserted into the urethra and can remain in place within the patient for several days. Diagnostic X-ray images can be taken with an X-ray imaging machine, as illustrated by the X-ray system 285 and the imaging detector 290. This confirms the position of the ring 202 in the prostate. Intraurethral ablation is performed when the positioning of the catheter is appropriate, and can be repeated and enlarged as necessary according to the description above. As stated above, the catheter can be left in place in the patient with the balloon inflated for several days after ablation until the ablated zone has fully liquefied. The catheter balloon can then be deflated, and the catheter removed from the urethra, whereupon the necrotic fluid from the ablation zone and the obliterated portion of urethral tissue will be washed away by the urine flow from the bladder B out the urethral channel.

One advantage of using a catheter-type ablation probe such as the embodiment shown in FIG. 5 is that minimal anesthesia is necessary in inserting the electrode into the urethra. Such catheter structures are familiar to urologists and can be inserted into the patient in the supine position with ease and comfort. A further advantage is that no endoscope is needed to insert it into the urethra or to visualize its position in the prostate. It can be used in an office setting, and not necessarily in a sterile operating room environment, thereby making the procedure more widely available to patients by reducing reduces hospital expenses. It is also relatively economical because it has low construction complexity and can thus be used disposably from a factory-packaged sterile pouch. A further advantage of the catheter structure is that the thermal element may be flexible or curvable. This will minimize discomfort, abrasion, bleeding, or other damage and morbidity to patients when the catheter is inserted through the penis and through the urethra as it curves up into the prostate. Thus, this embodiment has advantages of added safety, conformation to the urethra, and ease-of-use. A non-rigid catheter and non-rigid thermal element such as an RF conductive element or a resistive heating wire element or a laser diffusing element can be attached to the surface of the catheter or embedded within the wall of the catheter or integral within the flexible rubber structure of the catheter.

Figure 6:
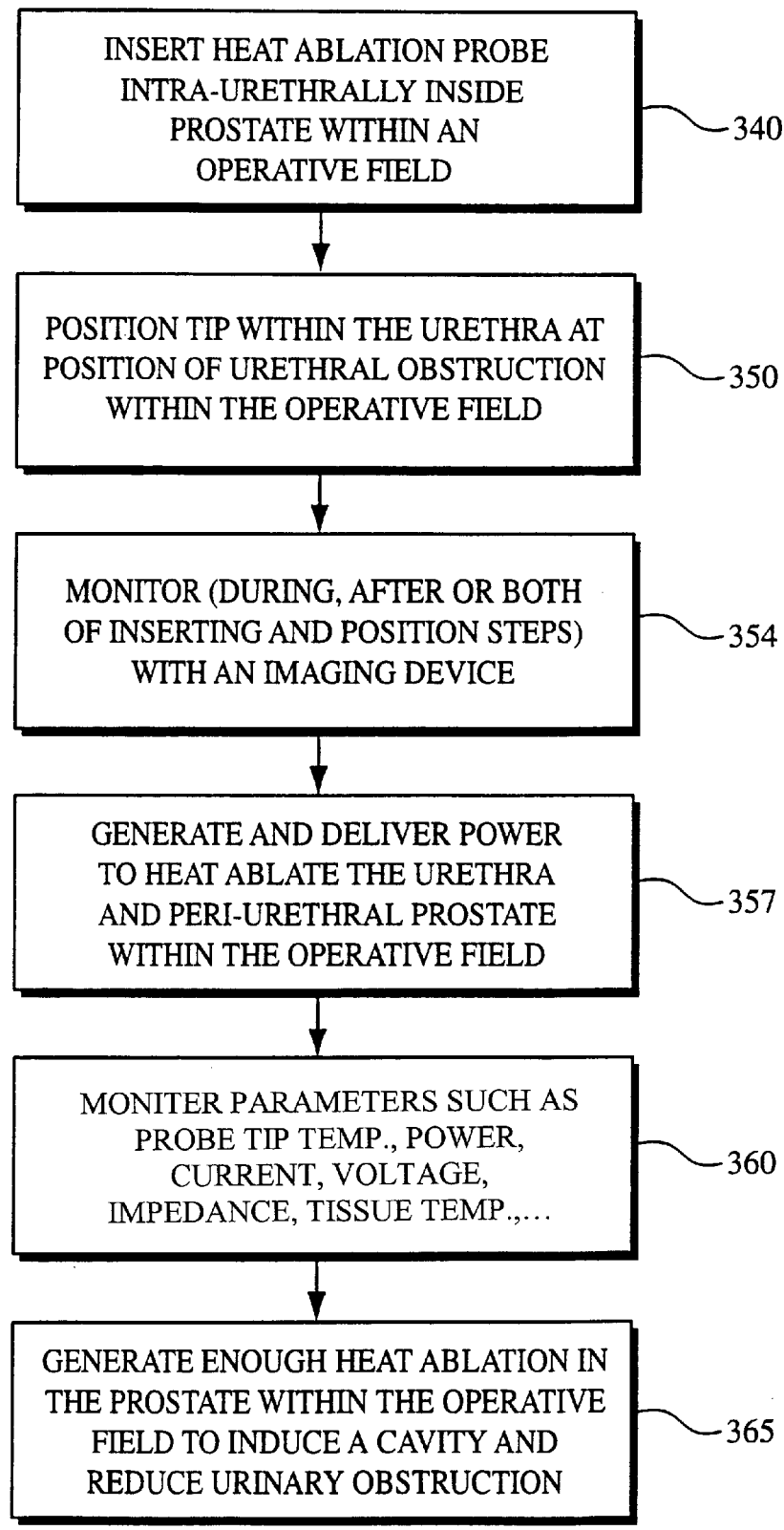
FIG. 6 shows a flow chart of the process employed in operating a system in accordance with the present invention.

Referring now to FIG. 6, a flow chart is shown to illustrate the process of intraurethral ablation for relief of urinary obstruction. The procedure starts by inserting the heating probe, such as any one of those described above, intraurethrally into the prostate (step 340), as illustrated in FIG. 1, for example. The positioning of the tip (e.g., the tip 2 of FIG. 1 or the element 202 of FIG. 5) within the urethra at the appropriate position of urethral obstruction is then performed (step 350). This step may involve the use of ultrasonic, CT, MR, or X-ray imaging measuring the electrode's depth in the urethra, the use of endoscopic visualization, or other positioning techniques. In the case of a balloon catheter, contrast injection into the balloon or the bladder followed by X-ray imaging is another way of positioning the RF tip in the appropriate position. The position of the tip in the urethra relative to the prostate is monitored (step 354). The use of CT, MR, ultrasound, X-rays, fluoroscopes, or other imaging devices may be used during this step, as they also may be used in the positioning step (step 350).

When the tip is in the proper position within the prostate, the step of generating and delivering power to heat ablate the urethra and periurethral prostate within the operative field is performed (step 357). This can involve elevating the voltage, current, or power applied by the resistive heating, laser, or high frequency generator. The generator may have manual controls such as knobs or other elements to control its output levels that can be actuated at this point. Alternatively, the process may be automated with a set power or temperature level predetermined on the generator control system and an automatic or semi-automatic achievement of that control parameter reached by an appropriate feedback and control system within the generator. These elements could all be built into the energy source 33, for example, illustrated in FIG. 1.

The actual parameters of the power delivered to the electrode within the urethra may be recorded and monitored (step 360). Parameters of interest can include the temperature recorded at the tip, the temperatures recorded at satellite electrodes placed in the prostate or in the neighboring operative field, the RF power, current, voltage, impedance, and so on. The time of power application may also be monitored at this step and a predetermined set time of exposure of the power to the electrode may be desirable, depending on clinical needs, or may depend on the reading of temperature sensors in the prostate or the probe at various positions. Knowledge of these parameters and the geometry and size of the probe tip assist in guiding the surgeon as to the size of the lesion and resultant urethral/prostatic cavity that is produced. For example, it may be known from clinical experience that certain size ablations can be induced for certain electrode geometry types with a known value of power, current, or voltage, or alternatively a known temperature as recorded in one or more of the temperature monitors. As represented in FIG. 6, these parameters may be monitored during the ablation process and influence the decision of the clinician to terminate or continue the process according to experience and parameter values. By reference, measurement of such parameters is accomplished by lesion generator systems of Radionics (Burlington, Mass.).

The adequacy of the duration and parameter sets to achieve the correct heat ablation in the prostate and to reduce urinary obstruction is determined (step 365). The decision to stop the procedure when it is believed that the cavity is adequate can be made in this step.

In accordance with one embodiment of the present invention, the clinician may choose a heating probe tip geometry of a certain size, diameter, length, or other characteristic. The clinician may know from experience that the insertion of such a probe intraurethrally with the probe having a temperature sensor and delivering power to raise the tissue temperature so that the tip is elevated to a certain temperature level will produce a known and generally adequate ablation cavity. This set of criteria may be used by the clinician to induce sufficient ablation sizes to alleviate urinary obstruction according to the clinical circumstances.

In accordance with another embodiment of the present invention, the probe may not include a temperature sensor. The correlation of ablation size desired for a given tip geometry may be determined by considering parameters such as power, output, voltage, and current. Generally, it can be determined that ablation temperatures of greater than 50° C. in the prostate tissue can be induced, for example, by power or current levels greater than known amounts. In that embodiment, these power and current parameters may be used by the clinician for a given time of ablation exposure to alleviate the urinary obstruction by creating a sufficient intraurethral cavity. It is understood that a range of these parameters and time exposures, as well as various probe geometries, may be used to grade the size of the ablation cavity according to the experience acquired by clinicians with this technique.

In accordance with one embodiment of the present invention, if CT, MR, or other imaging techniques are used during ablation, then they may be used to decide on adequate ablation size. For example, certain MR images can represent thermal distribution around the probe, and thus indicate the ablation zone.

Figure 7:
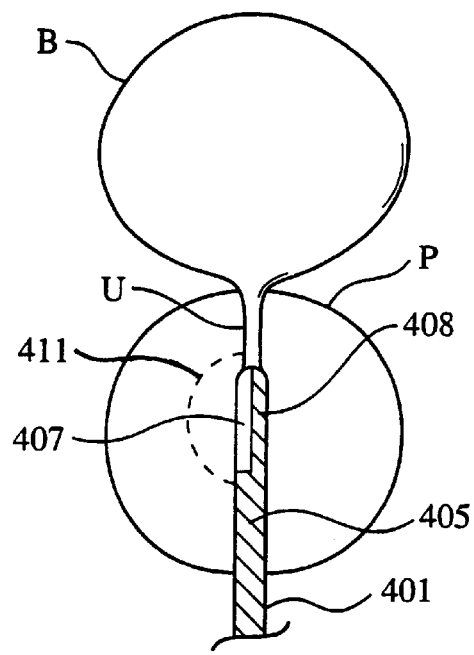
FIG. 7 shows another embodiment of a prostate ablation electrode according to the invention having an asymmetric thermal tip.

FIG. 7 illustrates another embodiment of the invention, in which the prostate P, the bladder B, and the urethra U are shown in partial sectional view. Probe 401 is inserted into the urethra U. As in various other disclosed embodiments, the electrode 401 has an insulated portion 405 (shown as hatched lines). However, an exposed conductive resistive heating element, laser diffuser, or tip 407 in this embodiment is asymmetrically configured at the end of the elongated probe 401. For example, the distal tip of the probe may have an insulated or covered side portion 408 to prevent that portion of the patient's urethra R from being exposed to heating from the generator (not shown in FIG. 7, but illustrated in FIGS. 1,4, and 5). The heating zone in this embodiment tends to lie proximate to the exposed tip portion 407. To illustrate an example ablation zone, a dashed line 411 is distributed laterally on a side of the urethra U corresponding to the exposed side portion 407 of the tip. The exposed side portion 407 may utilize various structures and/or shapes to suit various clinical uses, such as partial cylindrical surfaces, discrete areas of conductive exposure, lines or wires of exposed conductors, heating element, laser fibers on the electrode 401, and so on. This embodiment can be particularly advantageous when ablation should be directed asymmetrically to a particular portion of the patient's prostate.

Figure 8:
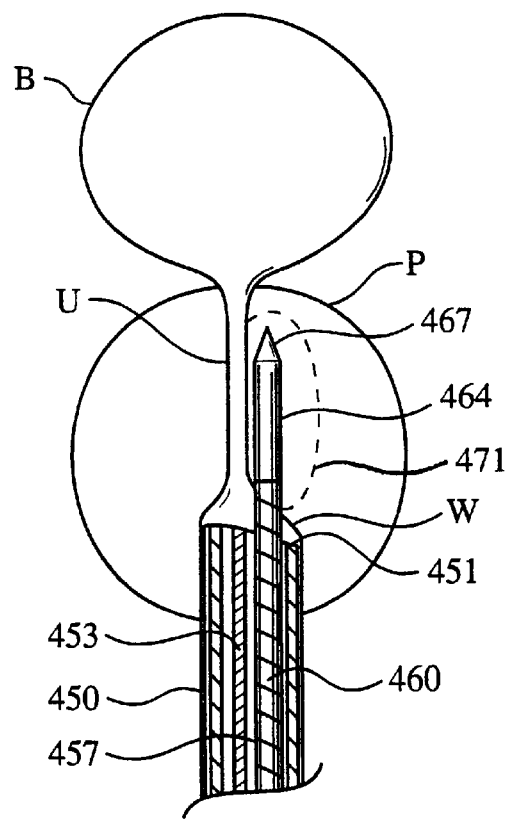
FIG. 8 illustrates another embodiment of prostate ablation probe according to the invention having a pointed thermal tip, which is adapted to be used in conjunction with a cystoscope.

FIG. 8 illustrates another embodiment of the invention, in which a cystoscope 450 is placed in the patients urethra U. A probe 457 is passed through the cystoscope shaft 450; it has an insulated portion 460 (shaded area). Tip 464 emerges from a distal end 451 of the cystoscope 450. The tip 464 defines a relatively sharp point 467, which is capable of piercing the urethra wall W. The tip 464 emerges approximately frontally from the cystoscope end 451, and it can be visualized by an optical channel 453 as it pierces the wall W. In this embodiment, connecting the tip 464 to the generator (not shown) will ablatively heat the prostate tissue near the tip 464. An ablation volume 471 (illustrated by a dashed line) around the tip 464 and can thereby be placed asymmetrically on one side of the urethra U to suit various clinical needs.

The use of intraurethral heat delivery probes herein has the advantages of simplicity, economy, control, consistency, reproducibility, and patient tolerance compared to other techniques aimed at treating BPH or prostate cancer such as TURP, TUNA, and other methods described above. In one embodiment of the present system and method, the tip is within the urethra, and does not pierce the urethral wall. As described, the heat ablation process using an intraurethral electrode according to the invention has the effect of ablating the urethral wall and periurethral tissue to open the channel and to destroy the urethra near the electrode. This has advantages over other methods and apparatus which seek to leave the urethra intact or unablated, such as TUNA or McGahan et al's procedure cited above. In one embodiment of the present invention, because the tip does not pierce the urethra, the risk of hemorrhage is reduced. Furthermore, with the tip within the urethra and under direct endoscopic visualization or other imaging control, there is a more exact knowledge of the ablation zone in the central prostate region to reduce the chance of damaging sensitive structures.

Also shown in FIG. 5, as an augmentation of the system, is an external coolant supply 273 with cooling connection(s) 271. This may supply cooled fluid such as saline to flow within a recirculating channel in catheter 201 to cool the electrode 202. Such cooling capability may or may not be included in the balloon catheter depending on clinical needs.

Figure 9:
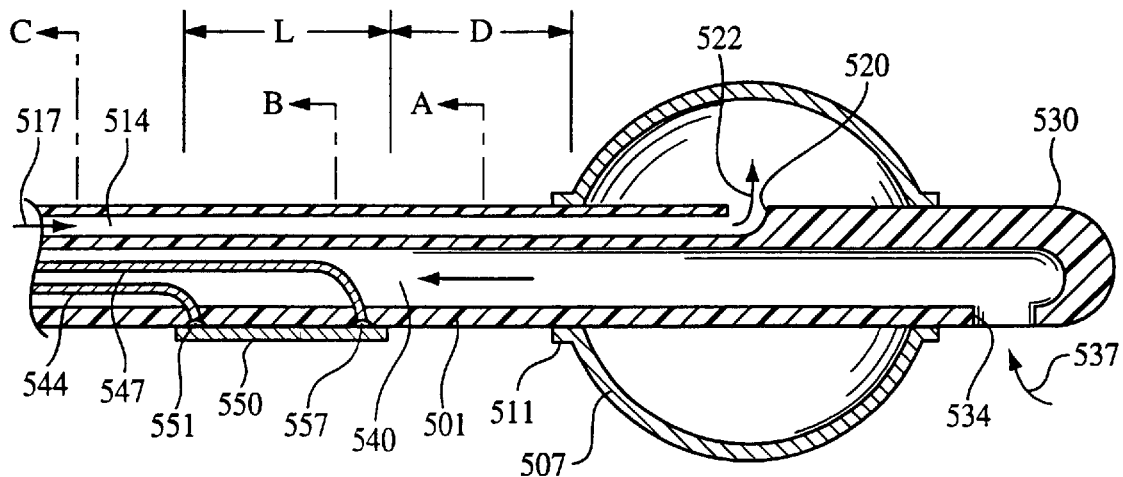
FIG. 9 shows a cross-sectional view of a balloon ablation catheter with resistive heater in accordance with the present invention.

Referring now to FIG. 9, a cross-sectional diagram illustrates various aspects of the distal end of a balloon ablation catheter in accordance with the present invention. This sectional view, which shows only the distal section of a catheter embodiment of the present invention, may correspond, for example, to a catheter similar to that in FIG. 5 described above. The catheter body 501 may be made of a rubber material such as silicone. It may be soft and flexible to accommodate the delicate urethral environment and the natural curves of the urethral path to the prostate. At the distal end is the inflated balloon 507, which also is made of a thin elastic rubber such as silicone. The balloon 507 may be secured in a sealed fashion by joints such as 511 to the catheter material 501. A channel 514 inside the catheter structure 501 allows an inflating fluid such as air or saline to fill the interior of the balloon 507. Injection of the fluid is indicated by the arrow 517, which may correspond to the influx of air as produced by the plunger system 260 in FIG. 5. The channel 514 may connect to the interior of the coupling hose 267 that attaches further to the inflating system 260 in FIG. 5. A side window 520 (i.e., port) in the wall of the catheter, but inside the balloon region, allows the in-flowing air to inflate the balloon, as indicated by the arrow 522.

At the distal tip 530 there is a hole in the body of the tip 534, which may correspond to the hole 217 in FIG. 5. When the catheter is inserted into the urethra and the balloon is secured within the bladder, as shown in FIG. 5, then urine can flow into the hole, as indicated by the arrow 537. An internal channel 540 is constructed within the body 501 of the catheter to allow the flow of the urine backwards towards the hub end of the catheter structure. For example, referring to FIG. 5, the channel 540 may be connected to the proximal hub 280 to allow the outflow of urine, as indicated by arrow F2.

A heating element 550 is shown in a location proximal to the balloon 507. This may be a resistive heating element, for example, a metal conductive high resistive wire, helix, braid, ring, or other structure which is bonded or mechanically fixed to the catheter rubber structure 501 with appropriate silicone cement. The length of the heating element 550 is indicated by L in FIG. 9. It is spaced by a distance D from the proximal portion of the balloon 507. The parameters L and D may be specified according to clinical needs and the particular anatomy of the patient being treated. For example, if it is known that a larger lesion is to be made because of a longer portion of urethral obstruction, then the length L could be made longer. The length of the heating element 550 may range from one to several millimeters, and even as much as a centimeter, or two, or more. The distance D may also be gauged depending on how far back from the neck of the prostate the heat ablation is desired to be located. D may also be a parameter which is specified according to clinical needs. For example, balloon catheters may come in various model numbers with specification of L and D and the diameter of the catheter body itself according to clinical criteria.

Heating or thermal element 550 may alternatively be a radiofrequency or high frequency electrode that has a conductive exposure on the surface of catheter 501. Element 550 may be a flexible structure such as a wire mesh helix, linear wire structure, conductive film made of plastic and embedded with conductive particulate matter, carbonized or metal embedded silicone rubber or other plastic elements, or segmented rings or strips of conductive material attached to the surface of the catheter 501 or embedded, linked, or stapled within a mass of the plastic comprising the catheter 501. In the case of a radiofrequency or microwave electrode, element 550 may be made of various metal or other conductive materials. Alternatively, element 550 may be a radiofrequency electrode of non-solid or non-uniform metallic construction that is integral with the wall of the catheter 501; for example a portion of silicone rubber embedded with conductive metal filings or carbon particles to make a portion of the catheter wall itself conductive without need for a separate metal plate, wire, braid, helix, or other solid metal ring.

Also shown in FIG. 9 are wire electrical connections 544 and 547. These connect to the heater resistive element 550. For example, wires 544 may be welded or soldered at point 551 to the resistor 550. The wires 544 and 547 may provide the connection to the generator 227 in FIG. 5 (i.e., they are contained in the cable 224). Also, electrical connection wire(s) 544 or 547 may be a thermal-sensing or impedance-sensing connection to a point 551 or 557 near or on the surface of electrode 550. For example, element 557 may contain a thermistor or thermocouple junction, and the connection cables 547 may be electrical connections to a thermal sensor (e.g., tissue monitor 237, FIG. 5) that enables readout of the temperature of prostatic tissue near 550 during the heating process. The electrical connectors 544 and 547, for example, may be directed within the channel 540 and branched through the rubber wall of the catheter at its proximal end to the connection 220, as shown in FIG. 1. Connectors 544 may connect to cables 224, and connectors 547 may connect to cables 234 and/or 224. It should be understood that the electrode 550 may consist of several segments as discussed herein. In this case, several connectors (544/547) may be used to connect to each segment of the electrode 550.

Current from the generator 227 in FIG. 5 is driven through wires 544 and 547 and through resistive element 550, which may have a high resistance compared to wires 544 and 547. This element 550 could be a high resistance wire coiled around the catheter body 501 or it could be a wire segment or plate attached to the wall of 501. It could have a thin plastic coating to bond well to 501 or to prevent sticking or reaction with the urethra.

In another embodiment, also illustrated by FIG. 9, the connectors 544 and 547 could be fiber optic laser light-carrying elements. They would bring laser light power from generator 227 to a diffuser element 550 in this illustration so that the laser power could be transmitted to the tissue outside of the probe 501.

Other physical techniques to provide heating power to the heating element 550 in order to ablate the urethra in accordance with the present invention could be desired by those skilled in the art. Use of microwave, magnetic, electromagnetic, ultrasound, or other power generators and associated connections in the probe are intended to be within the scope of the invention.

Figure 10:
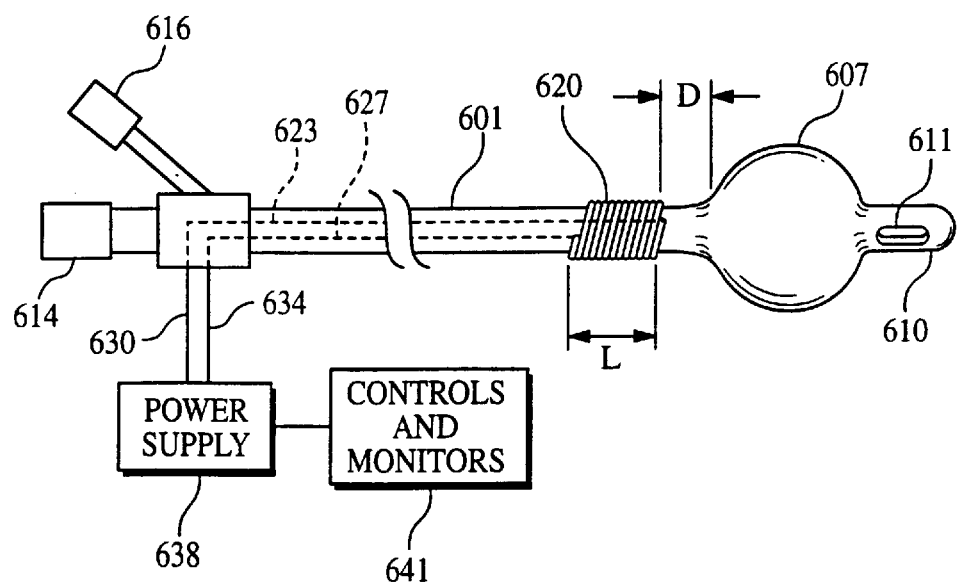
FIG. 10 shows a side view of a balloon ablation catheter with coiled heater element in accordance with the present invention.

Referring to FIG. 10, another embodiment of a balloon catheter with resistive heating element is shown in accordance with the present invention. The catheter tubing 601 is flexible. It could be made, for example, from silastic, polyurethane, or other materials. Balloon 607 is inflatable by inflation port 616, as described above. Catheter tip 610 has a drainage hole 61 1 which communicates to hub port 614. A thermal heater element 620 is fixed to the catheter and has length L and is set back by distance D from the balloon 607. Heater element 620 comprises a resistive heater wire which is wound in a helix on the catheter body 601. The heater coil is connected by internal conductors 623 and 627 to external connector cables 630 and 634 to the power supply 638. The power supply 638 generates current that runs through the coiled wire 620 to heat it up and ablate the urethra and nearby prostate tissue when implanted. Greater current from 638 will increase the temperature of heater 620 and make a larger ablation zone in the prostate. Thermal sensors can be placed near the coil 620 in the catheter to measure its temperature, and this can be read out on monitor 641. Controls on unit 641 can vary the power from supply 638 to vary the ablation size. Supply 638 could produce output from a few to several tens or hundreds of watts. Heater temperatures of 37° C. to near 100° C. could be achieved to produce ablation zones of a few millimeters to a few centimeters, according to clinical needs.

In an alternate embodiment represented by FIG. 10, element 620 may be an exposed coil of conductive wire that is connected to an RF power generator 638 to produce RF heating of the periurethral tissue.

Figure 11:
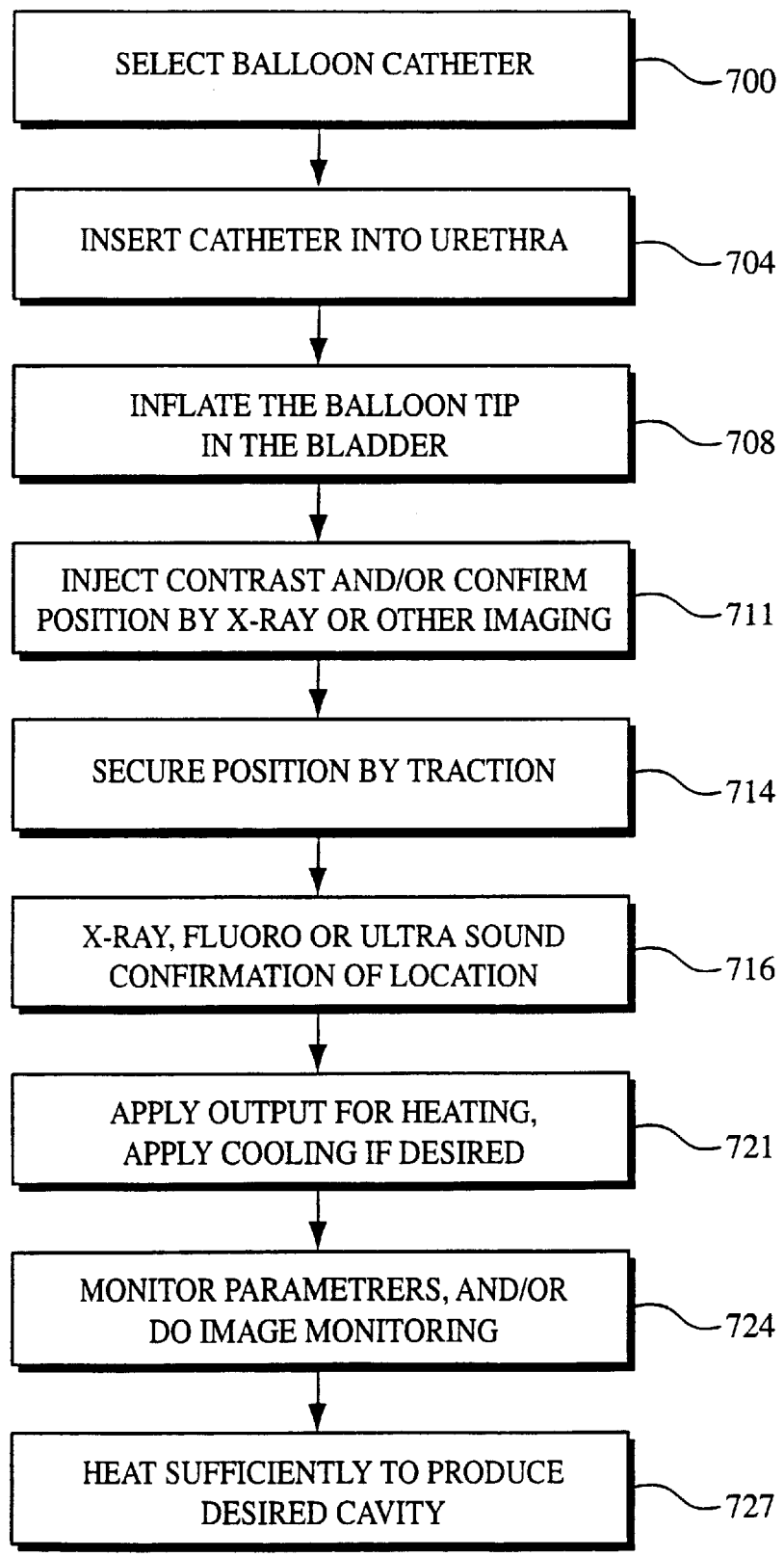
FIG. 11 shows a flow chart of a process employed in operating a system in accordance with the present invention.

Referring now to FIG. 11, a flow chart is shown to illustrate the process of intra-urethral RF ablation using a balloon catheter for relief of urinary obstruction. The procedure starts by selecting the appropriate balloon catheter (step 700). This may involve selecting the diameter, length, balloon size, ring dimensions and positions, use of multi-ring balloon catheter, use of catheters with temperature sensing, impedance monitoring rings, multiple temperature sensors along its longitudinal length, and other specifications of the balloon catheter, some of which have been described above. For example, by knowledge from diagnostic imaging of the size of the patient's prostate and the position of the obstruction, the appropriate length of RF electrode segment L, its separation D from the balloon may be selected. For this purpose, the catheters may come packaged with particular dimensions of L, D, catheter diameter, catheter length, etc. to suit specific clinical needs.

The next step may be insertion of the catheter into the urethra (step 704). Insertion of catheters is a common technique and can involve use of Foley-type catheters for urine drainage. During this step, diagnostic imaging such as ultrasound, CT, MRI, or X-rays may be used to monitor the position and depth of the catheter. For this purpose, the catheters as shown above may be in part radiopaque or have radiopaque markings on them so that their tip position and electrode position can be visualizable in X-ray, CT, MR, or other types of imaging.

Referring further to FIG. 11, once it is determined that the tip end of the catheter is properly within the patient's bladder, the balloon tip may be inflated within the patient's bladder (step 708 in FIG. 11). This step may be followed by further imaging (e.g., ultrasound, CT, MR, fluro, or X-ray diagnostic imaging) to confirm that the balloon is properly placed. For example, in step 711 of FIG. 11, a radiopaque contrast medium (contrast agent) is injected into the bladder through, for example, the hub 280 in FIG. 5 so that it emanates from the port opening 217 in FIG. 5 to produce a radiopaque contrast of the bladder. In this way, the position of the balloon within the bladder and against the neck AP in FIG. 5 can be confirmed. Alternatively, step 708 may involve inflating the balloon with radiopaque contrast fluid for X-ray confirmation.

The balloon may be secured in its position by applying traction or gentle pulling (step 714 in FIG. 11) so that the balloon fits snugly against the neck of the prostate and bladder junction. At this point, the element 202 is at a known position relative to the neck of the bladder. That position may be pre-selected by the dimension D, as shown in FIG. 9 or 10.

At this point, further X-ray, fluoroscopic, ultrasound, or other imaging confirmation may be used to verify that the probe and the balloon are in the proper place (step 716). When this confirmation is made, the connections to the external generator may be made as shown in FIG. 5, and the output from the generator 227 of FIG. 5 may then be delivered (step 721).

As the heat ablation process begins, the ablative destruction of the urethra and periurethral tissue will begin and increase near the position of the probe. This process can be monitored by observing the generator parameters on monitoring device 240 in FIG. 5 (step 724 of FIG. 11). Various other tissue monitoring such as temperature sensing and impedance monitoring at the heating element, probe, or ancillary rings such as 300 in FIG. 5 may be carried out in this step 724. The control of the generator may be done manually, automatically, or by computer, as in the control unit 228 of FIG. 5.

In step 727 of FIG. 11, the clinician determines the sufficiency of the heat ablation to produce the desired clinical effect of reducing urinary obstruction. This will be based on his experience, the visualization of the ablation parameters, and the particular clinical situation.

To elaborate further on the steps of making the heat ablation, the step 721 of FIG. 11 can involve elevating the voltage, current, or power applied by the generator. The generator may have manual controls such as knobs or other elements to control its output levels that can be actuated at this point. Alternatively, the process may be automated with a set power or temperature level predetermined on the generator control system and an automatic or semi-automatic achievement of that generator control parameter reached by an appropriate feedback and control system within the generator. These elements can all be built into the energy source 227, for example, illustrated in FIG. 5.

The actual parameters of the power delivered to the probe within the urethra may be recorded and monitored (step 724). The decision on the adequacy of the duration and parameter settings to achieve the correct heat ablation effect on the prostate that is sufficient to reduce urinary obstruction is determined at step 727 of FIG. 11. The decision to stop the procedure when it is believed that the cavity is adequate may also be made at this step.

Figure 12:
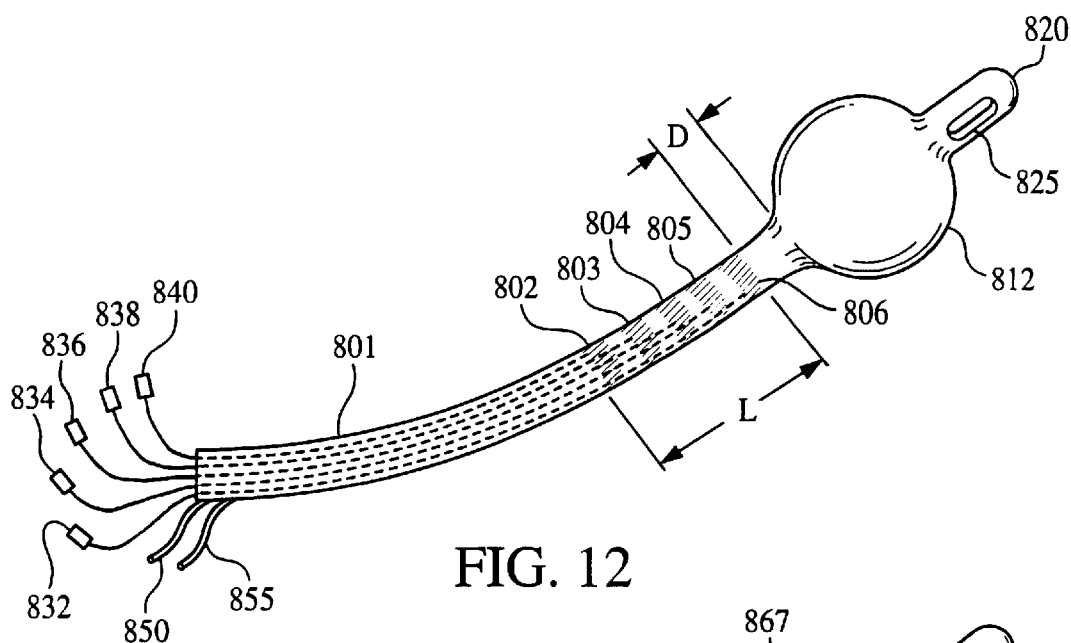
FIG. 12 illustrates another embodiment of the urethral probe according to the present invention having a flexible, segmented length of heating, thermal, or electrode elements.

Referring to FIG. 12, another embodiment in accordance with the present invention comprises a urethral catheter 801 that is flexible having thermal elements 802, 803, 804, 805, and 806 shown in sequence along its distal end. The first thermal element 806 is spaced a distance D from the balloon 812. Distance D can be preselected or variable to suit clinical needs. The segmented thermal elements 802 through 806 on the flexible catheter substrate produce a flexible region of thermal elements spanning the length L. This is convenient for insertion of the catheter in the urethra, since the urethra has a significant bend along its course toward the prostate. For the protection of the urethra, comfort of the patient, and minimization of potential untoward effects and injury, flexibility of the catheter may be desired for catheter insertion and manipulation procedures. The thermal elements 802 through 806 are connected to the external power source through connection elements 832, 834, 836, 838, and 840. These may be individual connections including, for example, power connections to resistive heating wires, electrical connections for high frequency or radiofrequency conductive elements, or connection of laser lines or other power source lines depending on the type of thermal elements 802 through 806 that is used.

The catheter 801 includes a distal tip 820 with a hole 825 for draining urine or inflating the bladder with fluid or contrast agent. Also shown is a balloon inflation channel 850, and a bladder drainage channel 855, which may communicate with the port 825.

Figure 13:
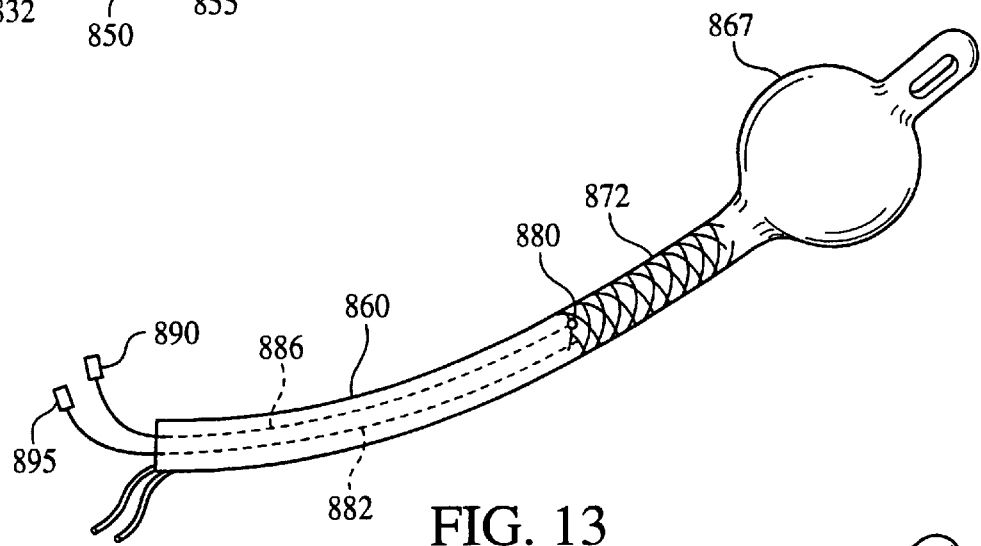
FIG. 13 shows another embodiment of the prostatic ablation system according to the present invention having a flexible, woven or braided thermal element.

Referring to FIG. 13, another embodiment in accordance with the present invention comprises a urethral catheter 860 with balloon structure 867 for anchoring into the bladder or prostate, and a thermal element or structure 872. Thermal structure 872 may be a braid of solid conductive wires that have a portion of surface exposure on the rubber catheter substrate 860. Alternatively, structure 872 may be a mesh or helix of conductive wires which may be partially embedded into the wall of the catheter 860 and partially exposed on the surface of the catheter 860. A thermal sensor 880 may be in proximity to thermal element 872 to sensor heating effects. Internal connections to the power source are illustrated, for example, by the dashed line 882, and thermo-sensing connection is illustrated by the dashed line 886. Connections of the external power source and monitoring system are illustrated by the connections 890 and 895. Thermal element 872 may also be a network of resistive heating elements which may not be conductively exposed to the urethra but rather be thermally exposed to the tissue to produce conductive heating out to the urethral wall and periurethral tissues.

Figure 14:
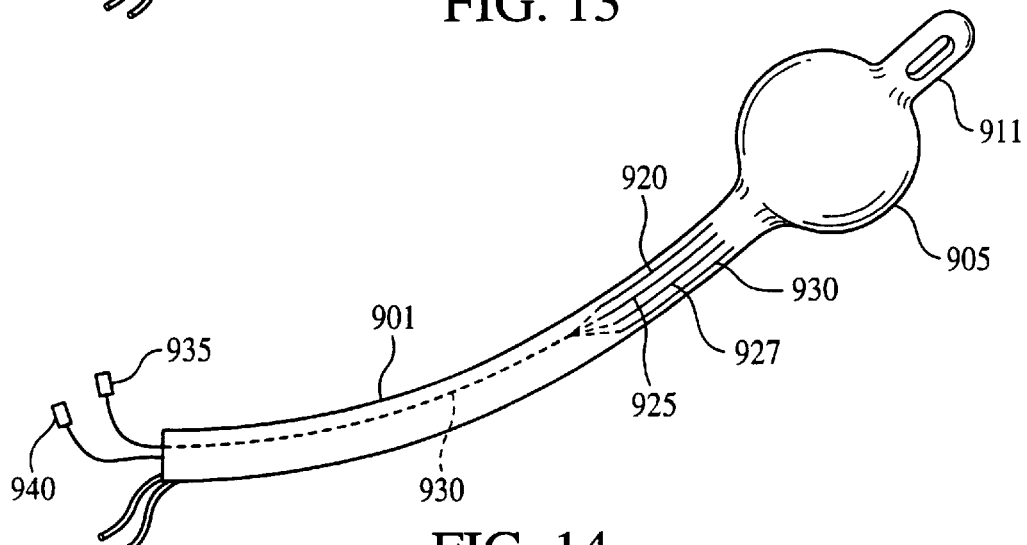
FIG. 14 shows another embodiment of a prostatic ablation system according to the present invention having a flexible series of linear longitudinal thermal elements.

Referring to FIG. 14, a flexible urethral catheter in accordance with the present invention has a rubber catheter body 901, a balloon structure 905, and a curved tip 911. The distal tip 911 may be curved to facilitate insertion of the catheter into the urethra which has natural curves as described above. Conventional curved tip balloon catheters are commercially available and referred to as Coude-tipped catheters. Also shown is an array of thermal elements illustrated by the curved, flexible, longitudinally linear elements 920, 925, 927, and 930. These may be exposed flexible metal wire structures which are woven into the wall of rubber catheter 901, fused or glued to the surface of the catheter 901, looped through the catheter wall in a threaded fashion so as to produce an array of flexible or conductive radiofrequency or microwave thermal elements. They may be connected in unison or connected individually by connection elements illustrated by the dashed line 930 to connections at the proximal end of the catheter where it is connected by connector 935 to an external power source or separate multiple power sources. Individual thermal sensors within the wire structures may be connected to an external monitoring system by connector 940. The linear thermal elements 920 through 930 may vary in their number, construction, width, and length. For example, thermal elements 920 through 930 may be made of flexible, braided stainless steel wire or other forms of metal. They may be resistive heating elements which are not conductively exposed to the tissue but have insulative sheets or coating over them and which are supplied with heating power from an external current source through the connection 935. The thermal elements 920 through 930 may be conductive, linear films or sheets that are attached to the surface of catheter 901. Thermal elements 920 through 930 may be integrated with the plastic material of the catheter 901 itself, such as silicone strips with carbonized or metallic particulate structure embedded within it and glued to the catheter 901.

Figure 15:
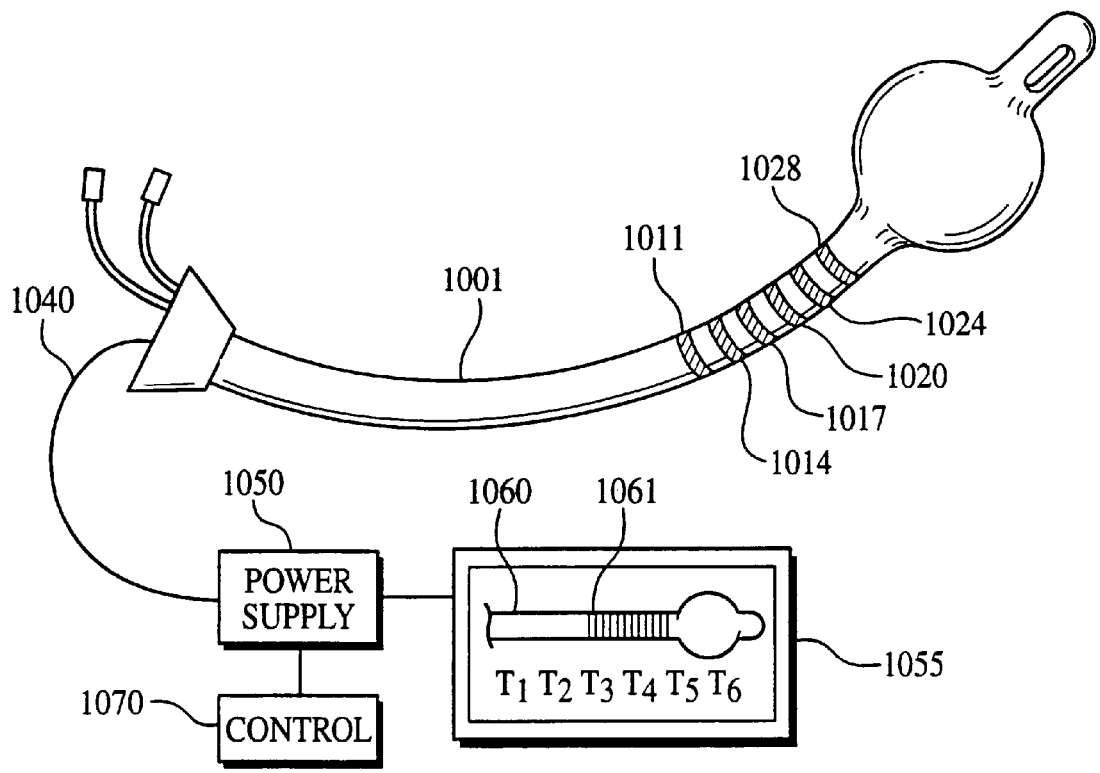
FIG. 15 shows another embodiment of a periurethral ablation electrode according to the present invention having a segmented series of azimuthal thermal elements near its tip end.

Referring to FIG. 15, an embodiment of the present invention is shown, including a flexible catheter 1001 having a series or an array of ring-like or azimuthal thermal elements 1011, 1014, 1017, 1020, 1024, and 1028 spaced in an array along the length of a segment of the catheter 1001. These ring structures may be, for example, conductive metal wire rings or metal annuli that are fixed to, glued to, or embedded in the surface or body of the rubber catheter 1001. Each of the rings 1011 through 1028 may include a temperature sensor. They may be electrically disconnected from each other, they may be connected in unison to form one equipotential surface, or they may be connected in selectable combinations to produce heating patterns around the elements to suit the size of the prostate or the region to be heated. Because of their separation and configuration, they may provide an extended length of conductive surfaces which are flexible and provide a bending curve in the location of their position on the catheter to facilitate insertion of the catheter into the urethra.

Also shown in FIG. 15 is a connection 1040 from the thermal elements 1011 through 1028 to a power source 1050, which may be a high frequency generator, a source of resistive heating in the case that the thermal elements are resistive heating elements, a laser power light source, or other form of power source. Also connected to the power source 1050 is a graphics display 1055, which has a graphic representation 1060 of the catheter structure 1001. Each of the thermal elements are also illustrated graphically, as for example element 1061 corresponding to the physical thermal element 1011 on the catheter. The generator control element 1070 may include selective connection alternatives to connect the power source to one, all or a sequence of the thermal elements 1011 through 1028. For example, for an extended length of periurethral ablation, all of the elements may be connected in unison. On the other hand, for a graded thermal lesion, only the first two elements 1028 and 1024 may be connected at the beginning of the treatment procedure. Later, elements 1022, 1017, 1014, and 1011 may be added to enlarge the length of urethral ablation. Alternating or varying connections in a bipolar or monopolar array of elements may be selected by the control 1070. This may be illustrated on the graphics display 1055 as the procedure carries on. For example, temperature readings from temperature sensors on one or more of the thermal elements may be illustrated by the numerals T1, T2, T3, T4, T5, or T6 shown on the graphics display. In this way the operator can enlarge, grade, and/or monitor the progression of the size and extent of thermal ablation in accordance with the present invention. The graphics display 1055 may have a graphic rendering or representation of the catheter that is shown at a glance in which thermal elements 1011 through 1028 are heating or activated. It may have control buttons and displays (not shown) to show power supply 1050 status, power output, impedance values on the elements such as 1011 to 1028, connection modes (monopolar/bipolar) and the like.

Figure 16:
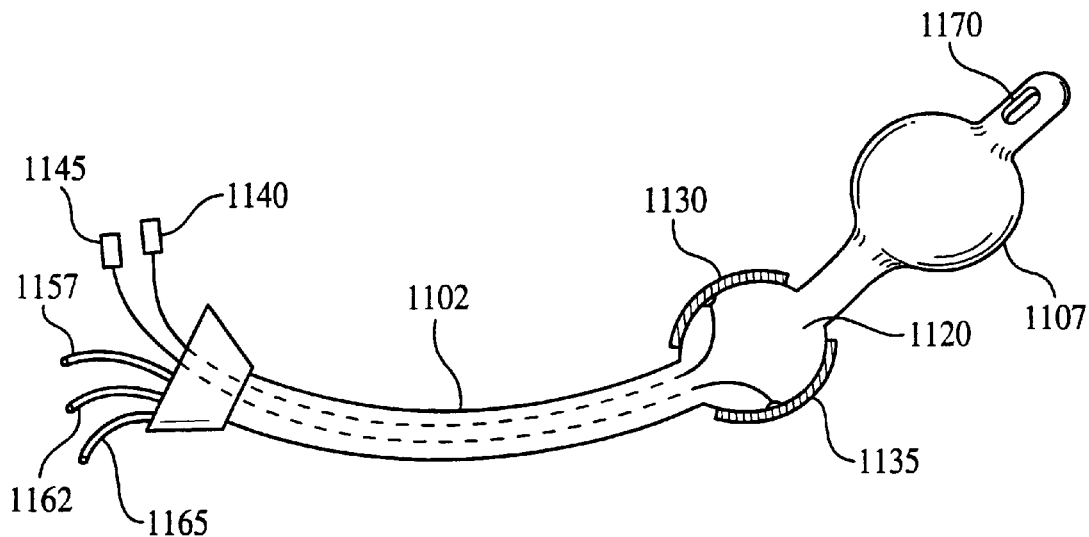
FIG. 16 shows another embodiment according to the present invention of a prostate ablation electrode comprising a balloon catheter with a second balloon incorporating a surface thermal element.

Referring to FIG. 16, a urethral catheter in accordance with the present invention has a flexible catheter structure 1102 with distal balloon 1107. A second balloon 1120 is proximal to the distal inflation balloon 1107. On the surface of balloon 1120 are thermal elements 1130 and 1135. The elements 1130 and 1135 may be conductive, exposed electrode sheets, wires, films, braids, or flexible materials that can be expanded with the expansion of balloon 1120 to form improved contact of, for example, an RF electrode to the urethral wall. The elements 1130 and 1135 may be spaced longitudinally or azimuthally on the balloon to suit clinical needs. The elements 1130 and 1135 may be connected to the external power source by connection elements 1140 an 1145. The distal balloon 107 may be inflated by air or fluid channel 1157 for anchoring within the bladder. Proximal balloon 1120 may be inflated by air or fluid channel 1162 to provide improved contact of the thermal element 1130 and 1135 to the urethral wall or to alter the shape of the thermal element 1130 and 1135. Channel 1165 may provide drainage or infusion communication to the bladder tip with its fluid opening 1170.

Figure 17:
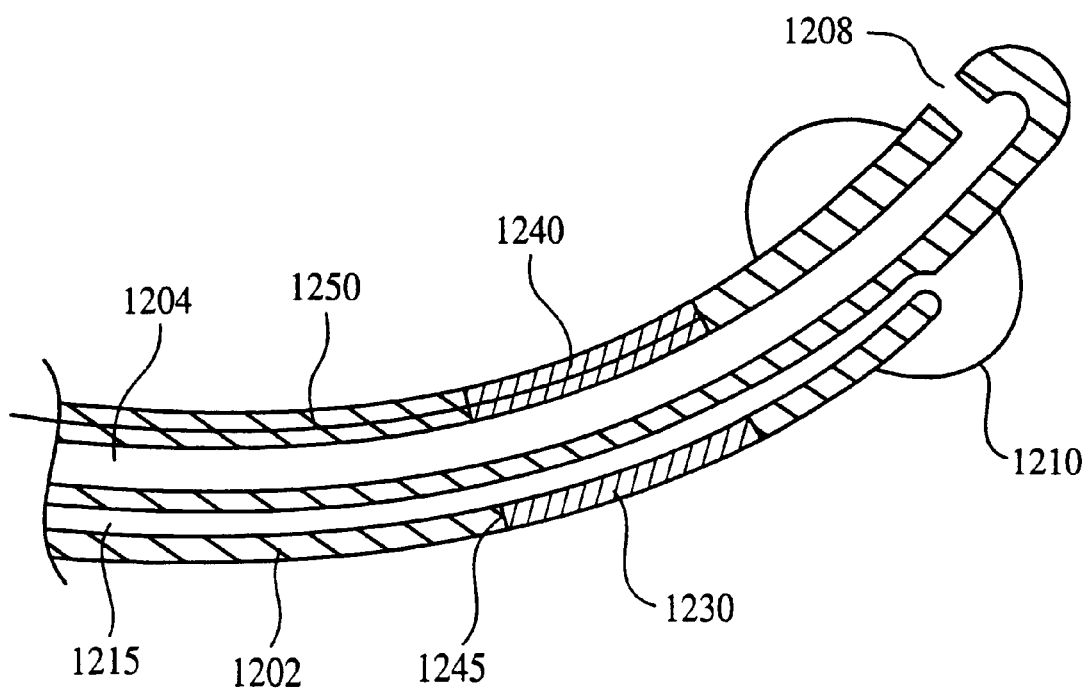
FIG. 17 illustrates another embodiment of a prostate ablation catheter tip in sectional view with a flexible thermal element integrated in a segment of the catheter wall.

Referring to FIG. 17, an embodiment of the present invention is illustrated in sectional view showing the distal portion of a flexible catheter having catheter wall structure 1202. A bladder communication channel 1204 is shown to distal tip hole 1208. Distal balloon 1210 is inflated by a fluid or air channel 1215. Within the walls of the catheter is a conductive or thermal heating element 1230 which may be symmetrically configured or may be connected to a similar thermal element 1240 on the opposing side or surrounding the catheter. The thermal elements 1230 and 1240 may be made of flexible rubber material with embedded, conductive particulate matter. For example, silicone rubber embedded with copper, steel, carbon, or other conductive material to form a flexible, conductive mass that can be bonded at an interface 1245 and 1247 to the rubberized catheter material 1202. Electrical connection from the rubberized, conductive portion 1230 and 1240 may be made by a conductive wire element 1250 that runs, for example, within the wall of the catheter 1202. Such an integral composite structure may provide the flexibility and the electrical conductivity for a thermal element for safety and convenience of application in the urethra. The thermal element may be an integral portion of the catheter wall itself. Thus, one need not use a separate metal plate, wire, or ring structure to achieve, for example, an RF conductive element.

Forms and embodiments of the urethral ablation system and method are provided involving various probe or electrode designs with and without temperature monitoring, and in various probe geometries. However, it should be recognized that other obvious forms may be used. For example, various materials, configurations, and control and display systems can be employed in a system or method for performing intra-urethral prostate ablation, with or without the capability of cooling the electrode, without departing from the scope of the invention. Various resistive heating materials and geometries could be devised. Heaters within probe tips or catheter rings and applicators can be devised. Various types, wavelengths, power ranges of lasers could be devised with various forms and types of laser transmission cables and emitter elements at the probe tip.

In view of these considerations, as would be apparent by persons skilled in the art, implementations and system should be considered broadly and with reference to the claims set forth below.

What is claimed is:

1. A method of relieving urethral obstruction in a patient having a urethra, a prostate and a bladder, the method comprising the steps of:

providing a catheter including:
a plurality of ring electrodes on an external surface of the catheter in a flexible region of the catheter configured and arranged to substantially maintain flexibility in the region, and
an inflatable balloon proximate to a distal end of the catheter wherein the inflatable balloon may be inflated by injection of fluid through a port in the catheter;

inserting the catheter into the urethra of the patient a distance sufficient to provide contact between the electrodes and at least a portion of the urethra and to insert the balloon into the bladder of the patient;

inflating the balloon;

positioning the electrodes within the urethra of the patient at a location in the prostate where urethral enlargement is desired; and applying a high-frequency signal to at least one of the electrodes to elevate the temperature to at least 50° C. and induce heat ablation of at least a portion of the urethra wall and at least a portion of periurethral tissue in the patient, thereby inducing ablative reduction of tissue mass of the urethra and nearby tissue to reduce the urethral obstruction.

2. The method of claim 1 wherein applying the signal includes enlarging the passageway relative to a normal size of the urethral passage.

3. The method of claim 1 wherein applying the signal includes applying the output through at least one of the electrodes to a return electrode.

4. The method of claim 1 including selecting one or more electrodes to be energized to grade a size of ablation.

5. The method of claim 1 wherein applying the signal includes energizing the electrodes in a bi-polar configuration.

6. The method of claim 1 wherein the step of providing includes at least one of the plurality of electrodes having a length greater than about 1 cm.

7. The method of claim 1 further comprising thereafter applying the high-frequency signal to a second electrode of the plurality of electrodes.

8. A method of treating the urethral passage, comprising:

placing a distal portion of an elongate member intraurethrally into the urethral passage, a flexible region of the distal portion of the elongate member having a plurality of ring electrodes on an external surface of a catheter configured and arranged to substantially maintain flexibility in the region, and energizing at least one of the electrodes with high frequency energy to elevate the temperature to at least 50° C. and ablate tissue of at least a portion of a wall defining the urethral passage and ablate adjacent prostate tissue to form a cavity communicating with the urethral passage.

9. The method of claim 8 wherein energizing at least one of the electrodes forms a cavity in the wall and adjacent prostate tissue having a diameter in the range of about 0.3 to 5 cm.

10. The method of claim 8 wherein energizing at least one of the electrodes elevates a temperature of the wall and adjacent prostate tissue to about 50 to 100° C.

11. The method of claim 10 wherein energizing at least one of the electrodes includes elevating the temperature for about six minutes.

12. The method of claim 8 wherein energizing at least one of the electrodes includes connecting the electrode to a high frequency generator.

13. The method of claim 8 wherein energizing at least one of the electrodes includes forming the cavity such that the urethral passage is enlarged relative to a normal size of the urethral passage.

14. The method of claim 8 wherein energizing at least one of the electrodes includes applying the high frequency energy through at least one of the electrodes to a return electrode.

15. The method of claim 8 further comprising imaging the electrodes to monitor the position of the electrodes.

16. The method of claim 15 wherein imaging includes ultrasonic imaging.

17. The method of claim 16 wherein imaging includes inserting an ultrasonic scanner transrectally.

18. The method of claim 15 wherein imaging includes CT imaging.

19. The method of claim 15 wherein imaging includes MR imaging.

20. The method of claim 8 further comprising detecting a temperature level of tissue surrounding the electrodes.

21. The method of claim 8 including selecting one or more electrodes to be energized to grade a size of ablation.

22. The method of claim 8 wherein energizing at least one of the electrodes includes energizing the electrodes in a bi-polar configuration.

23. The method of claim 8 wherein the step of providing includes at least one of the plurality of electrodes having a length greater than about 1 cm.

24. The method of claim 8 further comprising thereafter energizing a second electrode of the plurality of electrodes with the high-frequency signal.

25. A method of treating the urethral passage, comprising:

placing a distal portion of an elongate member intraurethrally into the urethral passage, a flexible region of the distal portion of the elongate member having a plurality of ring electrodes on an external surface of a catheter configured and arranged to substantially maintain flexibility in the region, each electrode being a non-cooled electrode, and energizing at least one of the electrodes with high frequency energy to elevate the temperature to at least 50° C. and ablate tissue of at least a portion of a wall defining the urethral passage and ablate adjacent prostate tissue to form a cavity communicating with the urethral passage.

* * * * *